(12) United States Patent
Omori

(10) Patent No.: US 9,173,548 B2
(45) Date of Patent: Nov. 3, 2015

(54) MEDICAL ROBOT SYSTEM

(71) Applicant: Karl Storz GmbH & Co. KG, Tuttlingen (DE)

(72) Inventor: Shigeru Omori, Ashigarakami-gun (JP)

(73) Assignee: Karl Storz GmbH & Co. KG (DE)

(*) Notice: Subject to any disclaimer, the term of this patent is extended or adjusted under 35 U.S.C. 154(b) by 0 days.

(21) Appl. No.: 13/950,382

(22) Filed: Jul. 25, 2013

(65) Prior Publication Data

US 2013/0310639 A1    Nov. 21, 2013

Related U.S. Application Data

(60) Division of application No. 13/761,824, filed on Feb. 7, 2013, now abandoned, which is a division of application No. 12/821,716, filed on Jun. 23, 2010, now abandoned, which is a continuation-in-part of application No. 12/327,189, filed on Dec. 3, 2008, now abandoned.

(30) Foreign Application Priority Data

Dec. 28, 2007   (JP) ................................. 2007-339211

(51) Int. Cl.
```
A61B 17/00      (2006.01)
A61B 1/00       (2006.01)
A61B 19/00      (2006.01)
A61B 17/29      (2006.01)
```
(52) U.S. Cl.
CPC .............. *A61B 1/00149* (2013.01); *A61B 19/22* (2013.01); *A61B 19/2203* (2013.01); *A61B 19/5212* (2013.01); *A61B 2017/2908* (2013.01); *A61B 2019/2223* (2013.01); *A61B 2019/2242* (2013.01); *A61B 2019/2276* (2013.01)

(58) Field of Classification Search
CPC ............... A61B 19/22; A61B 19/2203; A61B 2019/2242; A61B 1/00149; A61B 2019/2215; A61B 2019/223
USPC ........................................................... 606/1
See application file for complete search history.

(56) References Cited

U.S. PATENT DOCUMENTS

| | | | |
|---|---|---|---|
| 6,331,181 B1 | 12/2001 | Tierney et al. | |
| 6,889,116 B2 | 5/2005 | Jinno | |
| 7,608,083 B2 | 10/2009 | Lee et al. | |
| 7,930,065 B2 | 4/2011 | Larkin et al. | |
| 2008/0065100 A1 | 3/2008 | Larkin | |
| 2008/0262480 A1 | 10/2008 | Stahler et al. | |

FOREIGN PATENT DOCUMENTS

JP    8-52158 A    2/1996

(Continued)

*Primary Examiner* — William Thomson
*Assistant Examiner* — John R Downey
(74) *Attorney, Agent, or Firm* — Whitmyer IP Group LLC

(57) ABSTRACT

A medical robot system has a plurality of first robot arms supporting respective manipulators thereon; a second robot arm supporting an endoscope thereon; and a controller for controlling the first robot arms and the second robot arm. The manipulators and endoscope are inserted into a body cavity through a common trocar supporting member, wherein each of said manipulators includes a rod-shaped member for insertion through the trocar supporting member into the body cavity, a distal-end working unit mounted on a distal end of the rod-shaped member and having at least one joint, and at least one intermediate joint disposed in the rod-shaped member for bending said rod-shaped member.

2 Claims, 21 Drawing Sheets

(56) References Cited

FOREIGN PATENT DOCUMENTS

| | | |
|---|---|---|
| JP | 11-99124 A | 4/1999 |
| JP | 2002-102248 | 4/2002 |
| JP | 2003-61969 | 3/2003 |
| JP | 2003-127076 A | 5/2003 |
| JP | 2008-188113 A | 8/2008 |
| JP | 2008-237812 A | 10/2008 |
| JP | 2008-245840 A | 10/2008 |

21

MEDICAL ROBOT SYSTEM

CROSS-REFERENCE TO RELATED APPLICATIONS

This application is a divisional of and claims the benefit of priority from U.S. application Ser. No. 13/761,824, filed Feb. 7, 2013, which is a divisional of and claims the benefit of priority from U.S. application Ser. No. 12/821,716 filed on Jun. 23, 2010, which is a continuation-in-part of and claims the benefit of priority from U.S. application Ser. No. 12/327,189 filed Dec. 3, 2008, the entire contents of each of both of which are hereby incorporated by reference. U.S. application Ser. No. 12/327,189, claims the benefit of Japanese Patent Application No. 2007-339211, filed on Dec. 28, 2007.

BACKGROUND OF THE INVENTION

1. Field of the Invention

The present invention relates to a medical robot system using a medical manipulator having a distal-end joint operable by flexible members that are actuated by actuators.

2. Description of the Related Art

According to a laparoscopic surgical operation process, small holes are opened in the abdominal region, for example, of a patient, and an endoscope and manipulators or forceps are inserted into such holes. The surgeon performs a surgical operation on the patient with the manipulators or forceps, while watching an image captured by the endoscope and displayed on a display monitor. Since the laparoscopic surgical operation process does not require a laparotomy to be performed, the operation is less burdensome on the patient and greatly reduces the number of days required for the patient to spend in the hospital before recovering from the operation and being released from the hospital. Therefore, the range of surgical operations in which the endoscopic surgical operation process may be applied is expected to increase.

As disclosed in Japanese Laid-open Patent Publication No. 2002-102248 and Japanese Laid-open Patent Publication No. 2003-061969, a manipulator system comprises a manipulator and a controller for controlling the manipulator. The manipulator comprises an operating unit, which is manually operated, and a working unit replaceably mounted on the operating unit.

The working unit comprises a long joint shaft and a distal-end working unit (referred to as an "end effector") mounted on the distal end of the joint shaft. The operating unit has motors for actuating the working unit through wires. The wires have proximal end portions wound around respective pulleys. The controller energizes the motors of the operating unit to cause the pulleys to move the wires circulatively.

There has also been proposed a medical robot system for actuating medical manipulators with robot arms (see, for example, U.S. Pat. No. 6,331,181). The medical robot system can be remotely controlled by a master arm, and can be moved in various ways under a programmed control.

The medical robot system has the robot arms, which can selectively be used depending on the surgical technique required. One of the robot arms incorporates an endoscope therein for capturing an image representing the inside of a body cavity, which is capable of being visually confirmed on a display monitor.

According to the laparoscopic surgical operation process, it is desirable to provide a wider operative field in the body cavity being operated on of the patient because the wider operative field allows the manipulators to operate with greater freedom in the body cavity.

The body cavity may contain various organs in addition to the organ as the affected region, which make it difficult to provide a wide operative field in the body cavity. The manipulator on one of the robot arms of medical robot systems may be used as a retractor for retracting an organ or organs other than the affected region to a position out of interference with the surgical operation.

However, when the organ or organs are retracted by the retractor, the retractor itself may be positioned across the body cavity, and present itself as an obstacle in the operative field.

SUMMARY OF THE INVENTION

It is an object of the present invention to provide a method of using a medical manipulator which is capable of keeping a wide operative field in a body cavity.

A medical robot system according to the invention comprises a plurality of first robot arms supporting respective manipulators thereon; a second robot arm supporting an endoscope thereon; and a controller for controlling the first robot arms and the second robot arm. The manipulators and endoscope are inserted into a body cavity through a common trocar supporting member, wherein each of said manipulators includes a rod-shaped member for insertion through the trocar supporting member into the body cavity, a distal-end working unit mounted on a distal end of the rod-shaped member and having at least one joint, and at least one intermediate joint disposed in the rod-shaped member for bending said rod-shaped member.

According to a further feature of the invention, at least one of said manipulators in the medical robot system serves as a retractor, and the rod-shaped member of the at least one manipulator serving as the retractor includes a plurality of the intermediate joints.

According to a yet further feature of the invention, a monitor is provided for displaying an image captured with the endoscope; a first input means is operated by the left hand of an operator; and a second input means is operated by the right hand of said operator. When the rod-shaped members of two of the manipulators intersect with each other at the trocar supporting member, the manipulator that is located on the left side on a screen of the monitor is operated based on input operation by the first input means, and the manipulator that is located on the right side on the screen of the monitor is operated based on input operation by the second input means.

DESCRIPTION OF THE PREFERRED EMBODIMENTS

Figure 1:
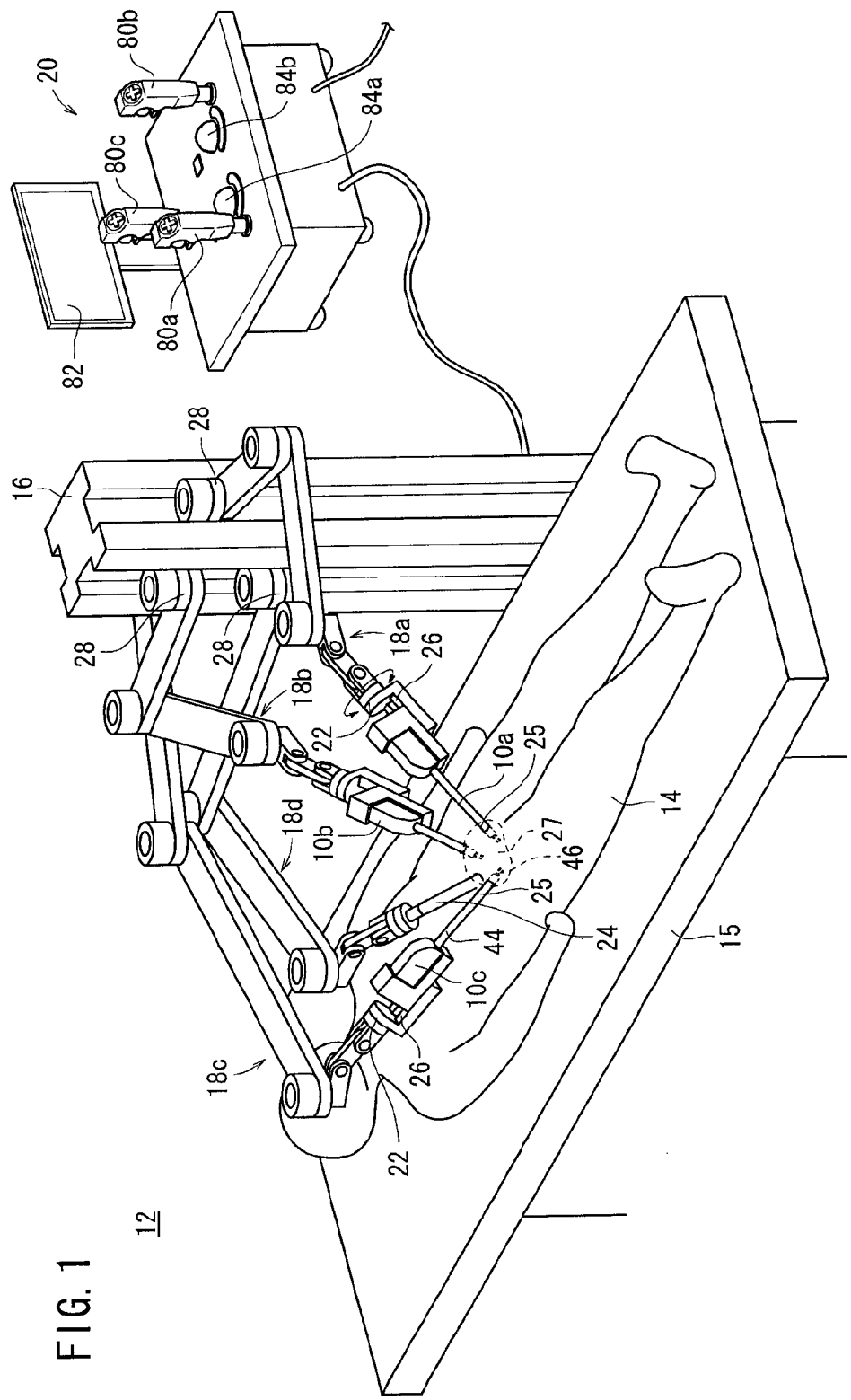
FIG. 1 is a perspective view of a medical robot system according to a first embodiment of the present invention.

Like or corresponding parts shall be denoted by like or corresponding reference characters throughout the views.

A medical manipulator and a medical robot system to be used according to embodiments of the present invention will be described below with reference to FIGS. 1 through 21.

As shown in FIG. 1, a medical manipulator $10c$ and a medical robot system 12 according to a first embodiment of the present invention are particularly suitable for performing a laparoscopic surgical operation on a patient 14.

The medical robot system 12 comprises a station 16 disposed near a surgical bed 15, four robot arms $18a$, $18b$, $18c$, $18d$ mounted on the station 16, and a console (controller) 20 for controlling the medical robot system 12 in its entirety. The robot arm $18c$ will also be referred to as a first robot arm, and the robot arm $18d$ as a second robot arm. The robot arms $18a$ through $18d$ and the console 20 may be connected to each other by a communication means comprising a wired link, a wireless link, a network, or a combination thereof. The console 20 is not required to control the medical robot system 12 in its entirety, but the robot arms $18a$ through $18d$ may be feedback-controlled by internal controllers combined with the medical robot system 12. The robot arms $18a$ through $18c$ may be actuated under the control of the console 20 for being operated according to automatic programmed operations or may be manually actuated by respective joysticks $80a$, $80b$, $80c$ on the console 20. The robot arms $18a$ through $18d$ also may be actuated through a combination of automatic programmed operations and manually controlled operations.

The robot arms $18a$ through $18c$ have manipulators $10a$, $10b$, $10c$ disposed respectively on distal ends thereof. The robot arm $18d$ has an endoscope 24 on the distal end thereof. The manipulators $10a$ through $10c$ and the endoscope 24 are inserted into a body cavity 27 of the patient 14 through respective trocars 25. The station 16 may comprise a plurality of stations supporting the respective robot arms $18a$ through $18d$. The manipulators $10a$ through $10c$ and the endoscope 24 are removably mounted onto the respective robot arms $18a$ through $18d$.

Each of the robot arms $18a$ through $18d$ has an articulated mechanism, e.g., a mechanism with six independent axes. The robot arms $18a$ through $18d$ are controlled by the console 20, so as to set the manipulators $10a$ through $10c$ and the endoscope 24 at arbitrary postures and at arbitrary positions, within the operating ranges of the robot arms $18a$ through $18d$. The robot arms $18a$ through $18c$ have respective joint mechanisms including rotary mechanisms 22 for rotating the manipulators $10a$ through $10c$ about respective joints shafts (rod-shaped members) 44.

The robot arms $18a$ through $18d$ have respective slide mechanisms 26 for moving the manipulators $10a$ through $10c$ and the endoscope 24 back and forth along the axes defined by the distal ends thereof, and respective lifting and lowering mechanisms 28, which are movable vertically along the station 16. The robot arms $18a$ through $18d$ may be structurally identical to each other, or may have different structures depending on the types of manipulators $10a$ through $10c$ and the endoscope 24 that are utilized.

The manipulators $10a$, $10b$ mounted respectively on the robot arms $18a$, $18b$ serve to perform direct surgical techniques on an affected region of the patient 14. A gripper, scissors, an electrosurgical knife, for example, are mounted onto distal-end working units of the manipulators $10a$, $10b$. The manipulator $10c$ mounted on the robot arm $18c$ comprises a retractor for retracting an organ in a body cavity 27 or the like to a given place to allow the surgeon to have a wider operative field.

Further structural details of the manipulator $10c$ and a joint between the manipulator $10c$ and the robot arm $18c$ will be described below. As shown in FIGS. 2 through 6, it is assumed that directions established with respect to the manipulator $10c$ include X directions representing horizontal transverse directions of the manipulator $10c$, Y directions representing vertical transverse directions of the manipulator $10c$, and Z directions representing longitudinal directions of the manipulator $10c$, i.e., a joint shaft (rod-shaped member) 44 thereof. The X directions include an X1 direction representing a rightward direction as viewed from the front of the manipulator $10c$ and an X2 direction representing a leftward direction as viewed from the front of the manipulator $10c$. The Y directions include a Y1 direction representing an upward direction and a Y2 direction representing a downward direction. The Z directions include a Z1 direction representing a forward direction and a Z2 direction representing a rearward direction.

Figure 2:
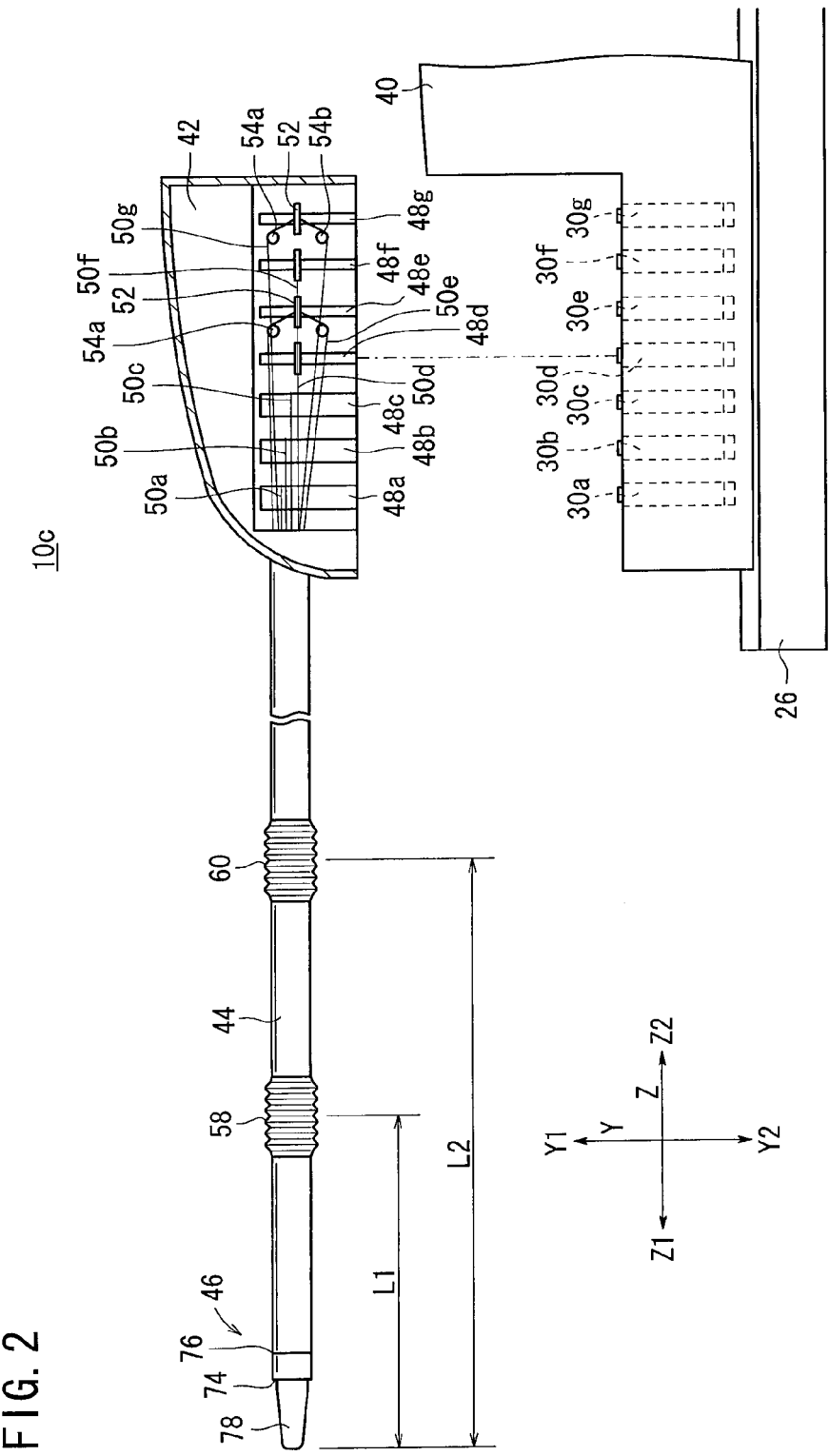
FIG. 2 is a side elevational view, partly in cross section, of a manipulator according to the first embodiment of the present invention.

As shown in FIG. 2, the manipulator $10c$ is removably mounted on a slider 40, which is disposed on the distal end of the robot arm $18c$. The slider 40 is slidable by the slide mechanism 26. The slider 40 supports seven motors $30a$, $30b$, $30c$, $30d$, $30e$, $30f$, $30g$ mounted therein in an array along the Z directions. The motors $30a$ through $30c$ (first actuator) serve to actuate a distal-end working unit 46, and the motors $30d$ through $30g$ (second actuator) serve to actuate a first intermediate joint 58 and a second intermediate joint 60.

The manipulator $10c$ comprises a connecting block 42 for connection to the slider 40, a hollow joint shaft 44 extending from the connecting block 42 in the Z1 direction, and a distal-end working unit 46 mounted on the distal end of the joint shaft 44.

The connecting block 42 is removably and replaceably mounted on the slider 40 by a removable mounting mechanism. The connecting block 42 supports pulleys $48a$, $48b$, $48c$, $48d$, $48e$, $48f$, $48g$ mounted thereon in an array along the Z directions and held in engagement with the respective motors 30a through 38g. The motors 30a through 30g or the pulleys 48a through 48g have noncircular teeth, while the pulleys 48a through 48g or the motors 30a through 30g have noncircular recesses. The noncircular teeth engage with the respective noncircular recesses for transmitting rotation of the motors 30a through 30g to the pulleys 48a through 48g.

Wires 50a, 50b, 50c, 50d, 50e, 50f, 50g are wound respectively around the pulleys 48a through 48g. The wires 50a through 50c (first flexible member) are annular in shape, wherein portions thereof are fixed to the pulleys 48a through 48c for preventing slippage on the pulleys 48a through 48c. The wires 50a through 50c are wound in 1.5 turns around the pulleys 48a through 48c, and extend in the Z1 direction inside the joint shaft 44. When the pulleys 48a through 48c are rotated about their own axes by the motors 30a through 30c, one of the two left and right turns of each of the wires 50a through 50c is wound around the pulley, and the other turn is paid out from the pulley. The wires 50a through 50c are spaced from each other in the Y directions so as to be held out of interference with each other.

The pulleys 48e, 48g have respective winding members 52 around which the wires 50e, 50g (second flexible member) are wound. The connecting block 42 houses therein pairs of idlers 54a, 54b for guiding the wires 50e, 50g from the winding members 52 to the joint shaft 44. The idlers 54a, 54b in the pairs are disposed in obliquely upward and downward positions that are spaced from the winding members 52 of the pulleys 48e, 48g in directions between the Z1 and Y1 directions and between the Z1 and Y2 directions, for guiding the wires 50e, 50g to upper and lower positions above and below the central axis of the joint shaft 44. When the pulleys 48e, 48g are rotated about their own axes by the motors 30e, 30g, one of the two upper and lower turns of each of the wires 50e, 50g is wound around the pulley, and the other turn is paid out from the pulley.

Figure 3:
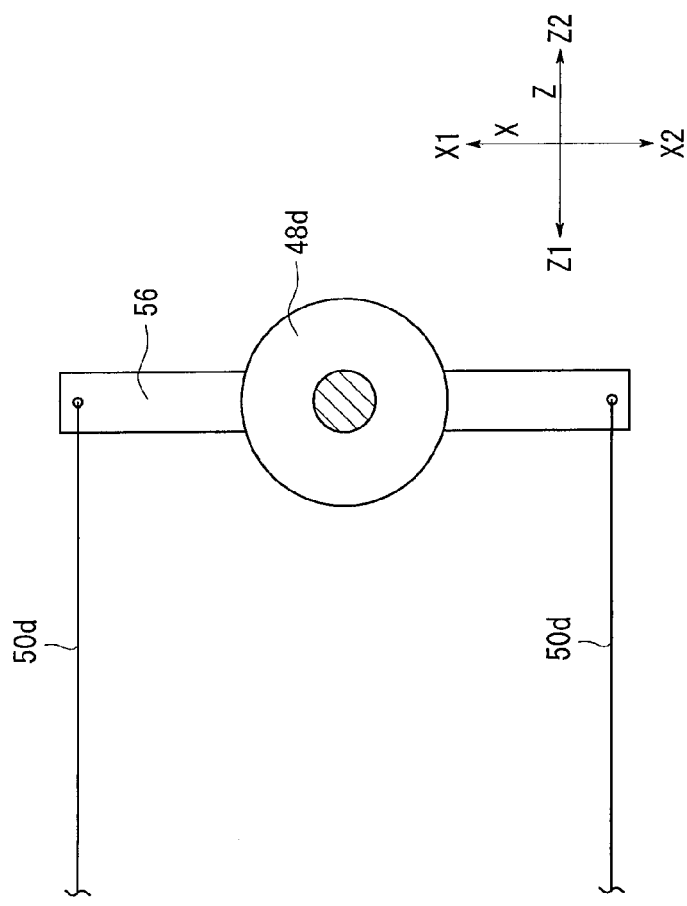
FIG. 3 is a plan view of a pulley and an arm.

As shown in FIG. 3, the pulley 48d has an arm 56 extending in the X directions, and the wire 50d has opposite ends connected to the respective ends of the arm 56. When the pulley 48d is rotated about its own axis by the motor 30d, one of the two left and right turns of the wire 50d is wound in, and the other turn is wound off. Although not shown, the pulley 48f and the wire 50f are of a structure identical to the pulley 48d and the wire 50d. As the wires 50d, 50f (second flexible member) are not wound around the pulleys 48d, 48f, the pulleys 48d, 48f do not operate as pulleys, but are referred to as pulleys for the sake of convenience.

As shown in FIG. 2, the joint shaft 44 extends from the connecting block 42 in the Z1 direction, and the distal-end working unit 46 is mounted on the distal end of the joint shaft 44. The joint shaft 44 has a first intermediate joint 58 and a second intermediate joint 60 which are successively spaced from the distal end thereof. The first intermediate joint 58 and the second intermediate joint 60 are bent when the wires 50d through 50g are displaced back and forth in the joint shaft 44. The first intermediate joint 58 may be located in any position (distance L1 in FIG. 2) within a range from 3 cm to 5 cm from the distal end of the joint shaft 44 including the distal-end working unit 46. The second intermediate joint 60 may be located in any position (distance L2 in FIG. 2) within a range from 7 cm to 12 cm from the distal end of the joint shaft 44 including the distal-end working unit 46. With the first intermediate joint 58 and the second intermediate joint 60 being thus positioned, the manipulator 10c suitably operates as a retractor in surgical techniques (see FIGS. 14 through 17) inside the body cavity 27.

Figure 4:
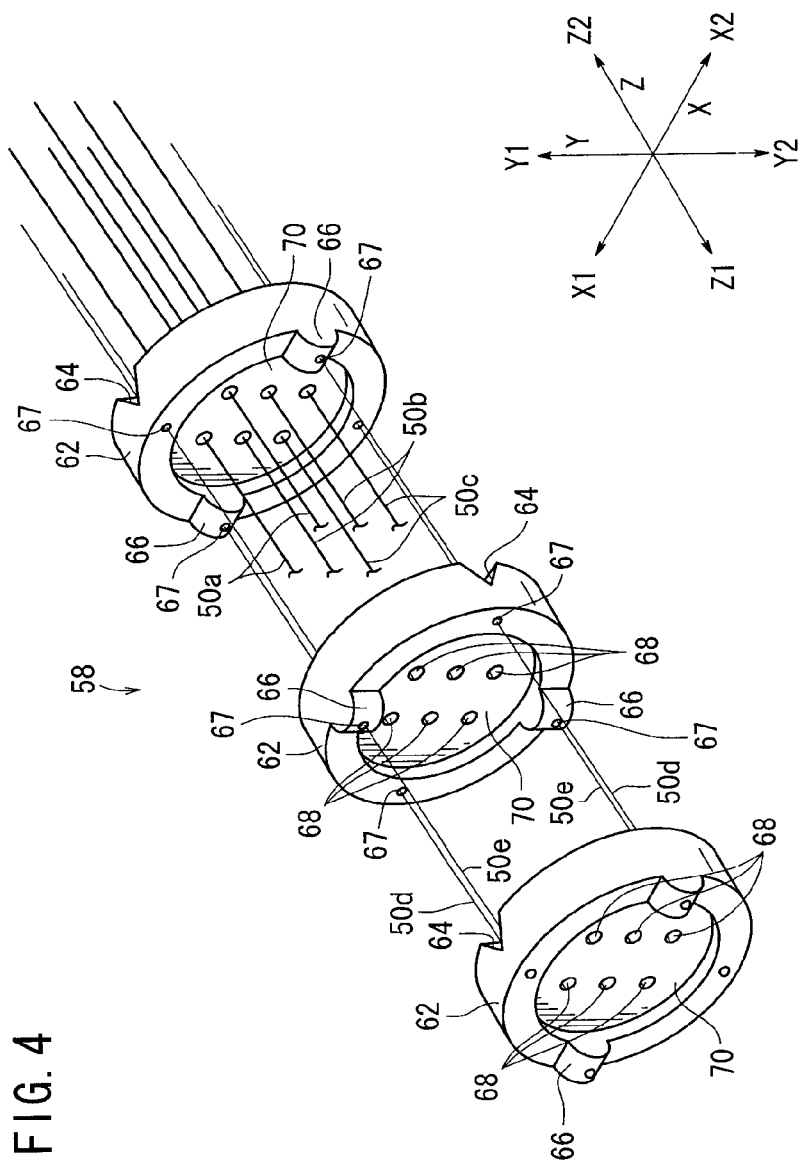
FIG. 4 is an exploded perspective view of a first intermediate joint.

As shown in FIG. 4, the first intermediate joint 58 comprises a stacked array of joint rings 62 that are angularly movable with respect to each other. In FIG. 4, the first intermediate joint 58 is shown as comprising three joint rings 62. However, the number of joint rings 62 is not limited to three, and the first intermediate joint 58 may comprise a suitable number of joint rings 62, e.g., 4 through 30 joint rings 62.

Each of the joint rings 62 has a pair of V-shaped grooves 64 defined in one surface thereof in diametrically opposite relation to each other across the center of the joint ring 62, and also has a pair of semicylindrical ridges 66 disposed on the other surface thereof in diametrically opposite relation to each other across the center of the joint ring 62. The grooves 64 and the ridges 66 are angularly spaced 90° from each other. Adjacent two of the joint rings 62 are arranged such that their pairs of grooves 64 are angularly spaced 90° from each other, and are also joined to each other such that the ridges 66 of one of the joint rings 62 are inserted in the respective grooves 64 of the other joint ring 62.

Each of the joint rings 62 has four through holes 67 defined therein at positions of the grooves 64 and the ridges 66. The wires 50d, 50e extend respectively through the through holes 67 in the joint rings 62 and have respective tip ends coupled to the joint ring 62 at the distal end side of the first intermediate joint 58 in the Z1 direction. The joint rings 62 are joined together into a substantially integral assembly.

With the ridges 66 being inserted in the respective grooves 64, gaps are left between the adjacent ones of the joint rings 62, allowing the ridges 66 to being angularly moved in the respective grooves 64. Therefore, the adjacent ones of the joint rings 62 can be angularly moved with respect to each other. Although the joint rings 62 of each adjacent pair are angularly movable through a small angle with respect to each other, the sum of the angles through which the joint rings 62 of all adjacent pairs are angularly movable is large enough to allow the first intermediate joint 58 to be bent through a desired angle, for example, in the range from about 60° to 120°. Accordingly, the distal-end working unit 46 can be bent into an orientation not parallel to the longitudinal axis of the joint shaft 44.

When the pulleys 48d, 48e are rotated a given angle about their own axes under the control of the console 20, the wires 50d, 50e are displaced back and forth by the corresponding distance for thereby bending the first intermediate joint 58 through a desired angle vertically and horizontally in a plane transverse to the joint shaft 44. In other words, the first intermediate joint 58 is bent or curved actively by being pulled by the wires 50d, 50e. The first intermediate joint 58 may be bent in desired directions and with a desired degree of freedom. Although not shown, the outer circumferential surface of each of the joint rings 62 may be covered with a layer made of an elastic or flexible material.

Each of the joint rings 62 has a central guide plate 70 having six guide holes 68 defined therein, through which the wires 50a, 50b, 50c extend. The six guide holes 68 are arranged in three pairs spaced apart in the Y directions, and are arrayed in two vertical rows spaced apart in the X directions. The six guide holes 68 are clustered near the central axis of the guide plate 70. When the first intermediate joint 58 is not bent, the wires 50a, 50b, 50c extending through the guide holes 68 are not bent, but extend straight. Although the joint rings 62 are shown as having the respective guide plates 70, at least one of the joint rings 62 may have a central guide plate 70.

When the first intermediate joint 58 is bent, the wires 50a though 50c are guided through the guide holes 68 against being unduly displaced or bent, and are held out of contact with each other and remain in respective appropriate positions.

Figure 5:
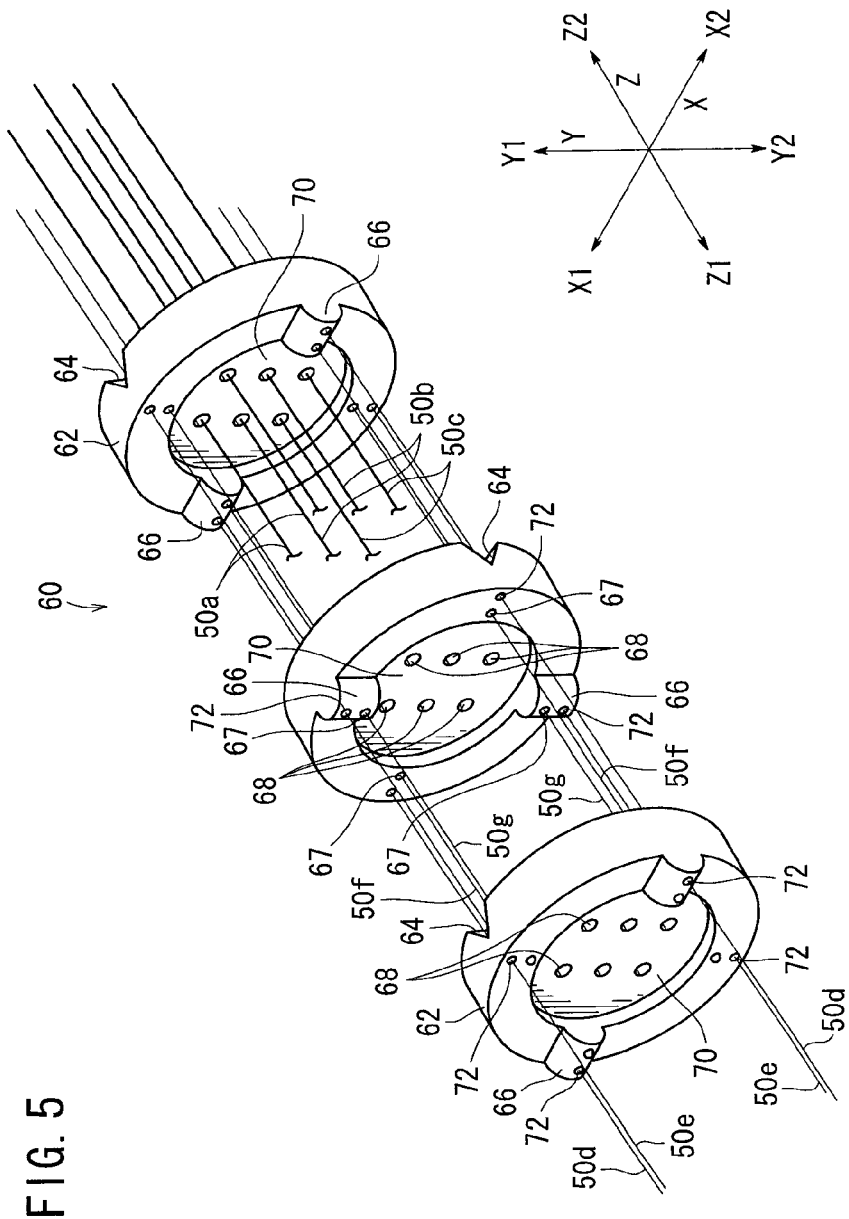
FIG. 5 is an exploded perspective view of a second intermediate joint.

As shown in FIG. 5, the second intermediate joint 60 is essentially identical in structure to the first intermediate joint 58, and comprises a stacked array of joint rings 62 each having four additional through holes 72 defined respectively adjacent to the four through holes 67. The wires 50f, 50g extend respectively through the through holes 67 in the joint rings 62, and act in the same manner as the wires 50d, 50e in the first intermediate joint 58, for actively bending or curving the second intermediate joint 60. The wires 50d, 50e extend respectively through the through holes 72 and further extend toward the first intermediate joint 58 in the Z1 direction.

The first intermediate joint 58 and the second intermediate joint 60 are covered with respective bellows-like or flexible and bendable sheaths. The other portion of the joint shaft 44 than the first intermediate joint 58 and the second intermediate joint 60 is made of a hard material.

Figure 6:
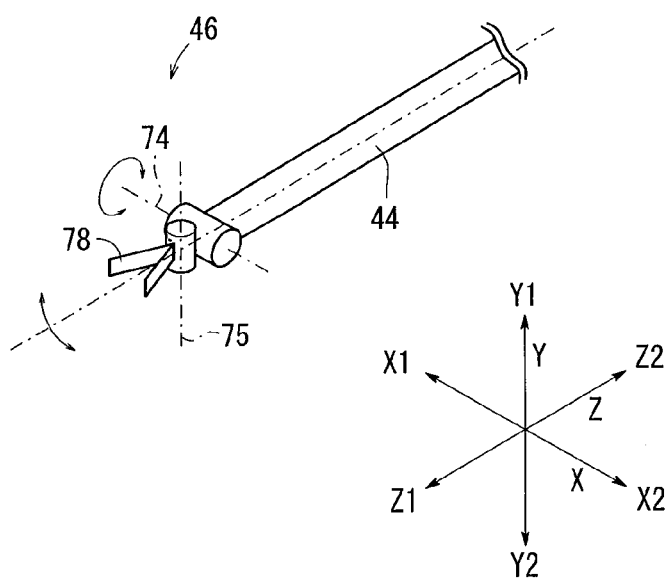
FIG. 6 is a perspective view of a distal-end working unit.

As shown in FIG. 6, the distal-end working unit 46 is mounted on the distal end of the joint shaft 44, and comprises at least a pulley (rotor) around which the wire 50a is wound, a pulley around which the wire 50b is wound, and a pulley around which the wire 50c is wound. When the wires 50a, 50b, 50c are moved back and forth upon rotation of the pulleys 48a, 48b, 48c in the connecting block 42, the pulleys in the distal-end working unit 46 are driven to rotate, causing the distal-end working unit 46 to move about three axes. The motions of the distal-end working unit 46 include angular motions about a pitch axis (distal-end joint) 74 and a yaw axis (distal-end joint) 75 and opening and closing motions of a gripper 78, for example. The gripper 78 comprises a pair of gripper arms, one or both of which are openable. The distal-end working unit 46 may be of the same mechanism as the distal-end working unit of the medical manipulator disclosed in Japanese Laid-Open Patent Publication No. 2003-061969, for example.

Since the first intermediate joint 58, the second intermediate joint 60, the pitch axis 74, the yaw axis 75, and the gripper 78 can possibly cause a mutual interference, the console 20 calculates an amount of interference and controls the wires 50a through 50g to move back and forth to compensate for an interfering movement. In other words, the console 20 controls the wires 50a through 50g such that when it moves one of the movable members, it prevents the other from unnecessarily moving due to such an interfering movement.

The manipulators 10a, 10b may be of a structure which is free from the first intermediate joint 58, the second intermediate joint 60, the motors 30d through 30f, the wires 50d through 50f, and the pulleys 48d through 48f of the manipulator 10c, and which is otherwise the same as the manipulator 10c. Alternatively, the manipulators 10a, 10b may be structurally identical to the manipulator 10c.

Figure 7:
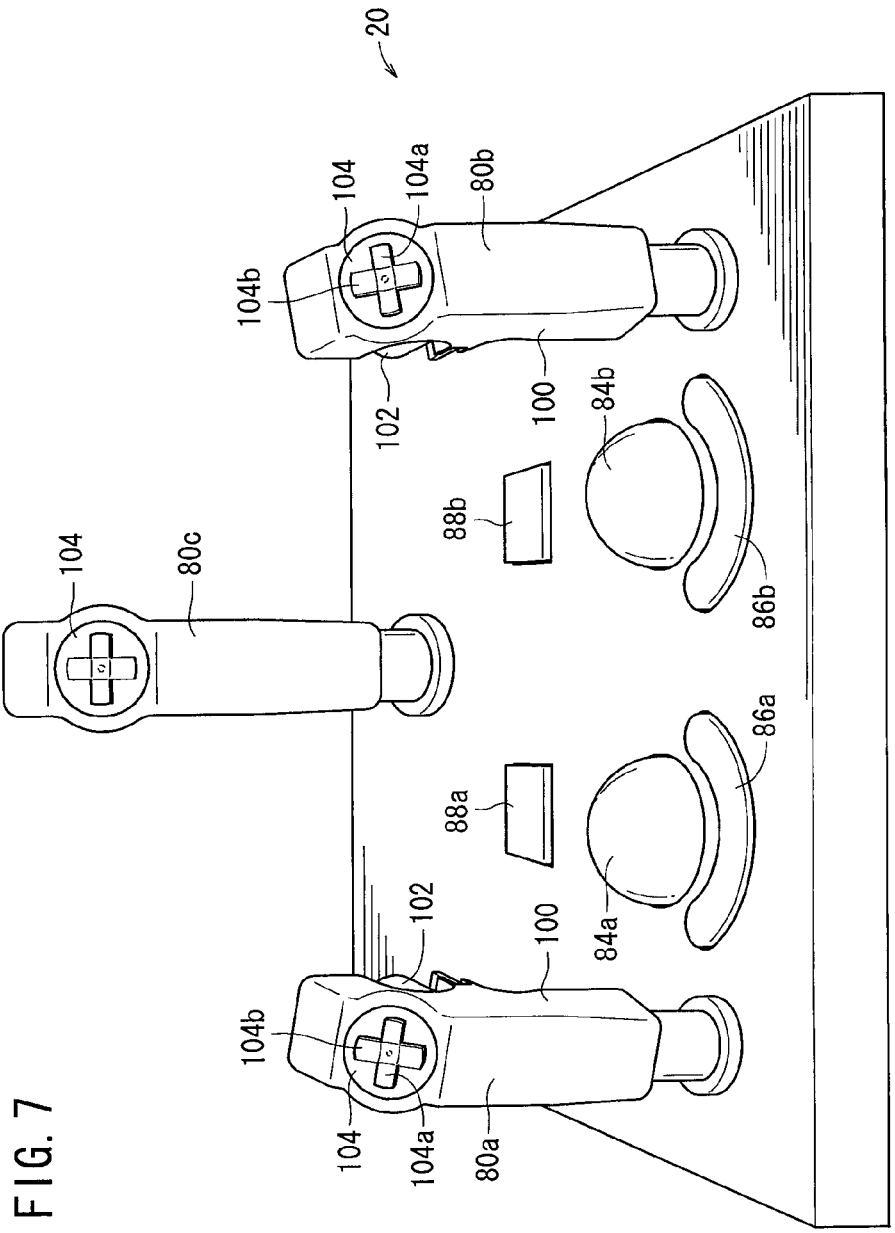
FIG. 7 is a perspective view of a console.

As shown in FIG. 7, the console 20 has three joysticks 80a, 80b, 80c as manual control units, a display monitor 82 (see FIG. 1), two trackballs (rotary input means) 84a, 84b, enable switches 86a, 86b for enabling or disabling input actions of the trackballs 84a, 84b, and return switches 88a, 88b. The display monitor 82 displays information about an endoscopic image captured by the endoscope 24 and other information. The trackballs 84a, 84b are spaced from each other at a central area on the upper surface of the control table of the console 20. The return switches 88a, 88b are disposed behind the respective trackballs 84a, 84b. The enable switches 86a, 86b comprise arcuately-shaped momentary switches disposed around respectively partly circumferential surfaces of the trackballs 84a, 84b.

The operator can operate the joysticks 80a, 80b, 80c to move the robot arms 18a, 18b, 18c individually. The robot arm 18d can be operated by another input means, not shown.

The joysticks 80a, 80b are positioned at respective left and right positions where they can easily be operated by the operator. The joystick 80c is positioned in a central position behind the joysticks 80a, 80b.

The joysticks 80a, 80b, 80c are vertically movable, twistable, and tiltable in all directions for moving the robot arms 18a, 18b, 18c according to the joystick motions. When the joysticks 80a, 80b, 80c are released from the hands of the operator, they automatically return to their upright reference orientations shown in FIG. 7 with the robot arms 18a, 18b, 18c being kept in their displaced positions. The joysticks 80a, 80b, 80c are basically identical in structure to each other, and have a handle grip 100 which is gripped by a human hand, a trigger lever 102 which is pushed and pulled mainly by an index finger and a middle finger, and a composite input pad 104 which is gripped mainly by a thumb. When the trigger lever 102 is operated, the gripper 78 is opened and closed. The composite input pad 104 includes horizontal and vertical see-saw switches 104a, 104b disposed centrally thereof in a crisscross pattern. When the horizontal see-saw switch 104a is operated, the distal-end working unit 46 is tilted about the yaw axis 75, and when the vertical see-saw switch 104b is operated, the distal-end working unit 46 is tilted about the pitch axis 74.

The robot arms 18a, 18b, 18c can be operated in an absolute coordinate (world coordinate) operation mode and a tool coordinate operation mode, for example.

In the absolute coordinate operation mode, the manipulator 10c coacts with the robot arm 18c (including the slide mechanism 26) connected thereto based on an input action of the joystick 80c. At this time, the position of the distal-end working unit 46 is set based on absolute coordinates depending on the movement of the handle grip 100, and the orientation of the distal-end working unit 46 is set based on input actions of the see-saw switches 104a, 104b.

In the tool coordinate operation mode, the manipulator 10c coacts with the robot arm 18c (including the slide mechanism 26) connected thereto based on an input action of the joystick 80c, for moving the distal-end working unit 46 back and forth in a constant posture based on a tool coordinate system according to the posture of the distal-end working unit 46.

Figure 8:
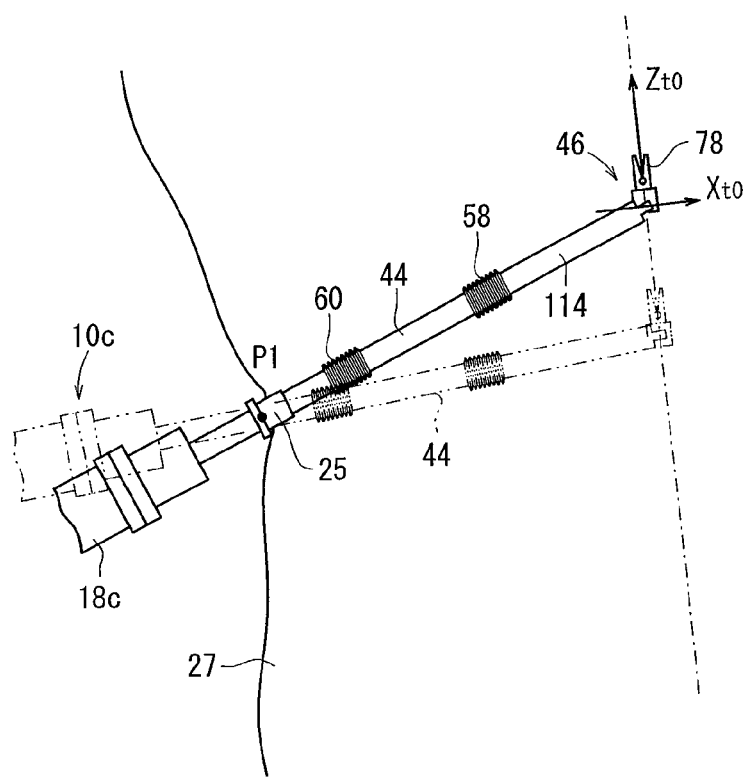
FIG. 8 is a view illustrative of a tool coordinate operation mode.

For example, as shown in FIG. 8, according to the posture of the distal-end working unit 46 at the time, a tool coordinate system having orthogonal axes $Zt_0$, $Xt_0$, $Yt_0$ (the axis $Yt_0$ is omitted from illustration) is established, and the distal-end working unit 46 is operated based on the established tool coordinate system. The distal-end working unit 46 is moved from an imaginary-line position to a solid-line position while the gripper 78 is extending along the coordinate axis $Zt_0$. At this time, the position of a hypothetical reference point P1 at the trocar 25 (pivot point) and the posture of the distal-end working unit 46 are kept constant.

Figure 9:
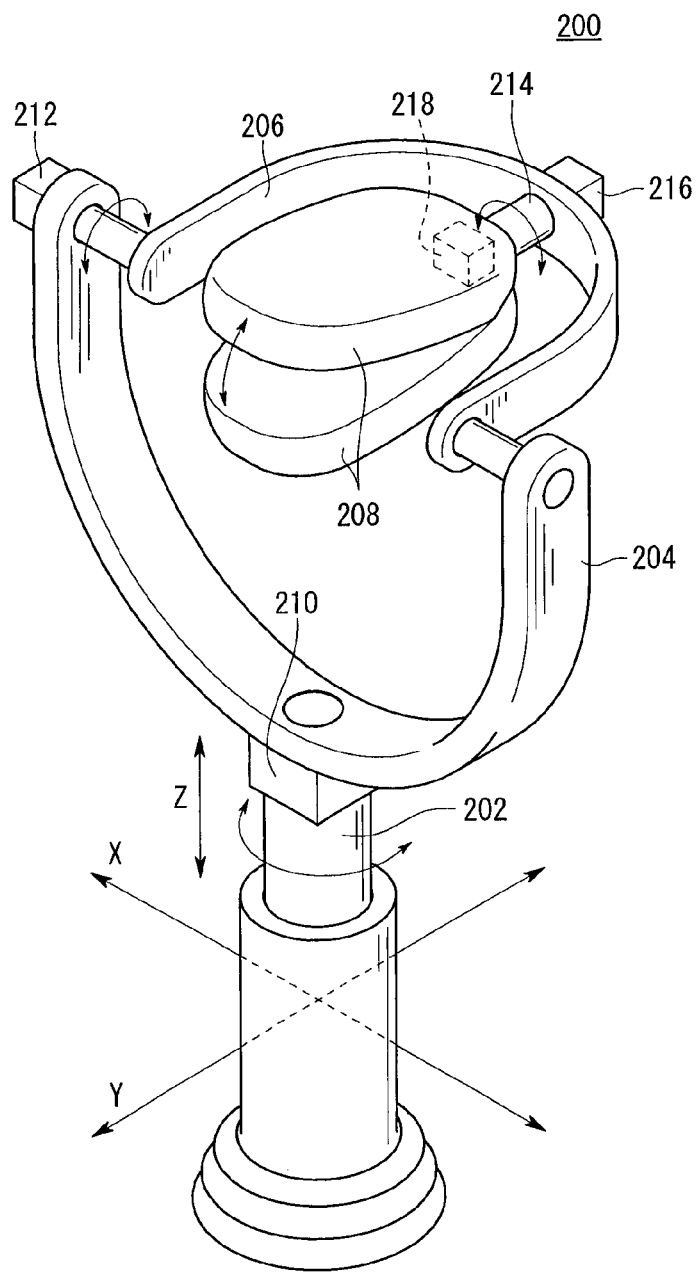
FIG. 9 is a perspective view of a master arm.

The joysticks 80a, 80b, 80c may be replaced with a master arm 200 shown in FIG. 9.

As shown in FIG. 9, the master arm 200 comprises a pivot shaft 202, a first U-shaped member 204, a second U-shaped member 206, and a pair of tongue members 208. The first U-shaped member 204 is open upwardly and rotatably mounted on the upper end of the pivot shaft 202 for rotation in a horizontal plane. The angle through which the first U-shaped member 204 is rotated with respect to the pivot shaft 202 is detected by a rotation sensor 210 and reflected in the motion of the distal-end working unit 46 about the yaw axis 75.

The second U-shaped member 206 is smaller in size than the first U-shaped member 204, and is disposed in the first U-shaped member 204. The first U-shaped member 204 and the second U-shaped member 206 have their ends rotatably connected to each other. The second U-shaped member 206 is rotatable in a vertical plane with respect to the first U-shaped member 204. The angle through which the second U-shaped member 206 is rotated with respect to the first U-shaped member 204 is detected by a rotation sensor 212 and reflected in the motion of the distal-end working unit 46 about the pitch axis 74.

The tongue members 208 are rotatably mounted on an intermediate portion of the second U-shaped member 206 by a shaft 214. The angle through which the shaft 214 is rotated with respect to the second U-shaped member 206 is detected by a rotation sensor 216 and reflected in the operation of the rotary mechanisms 22 (see FIG. 1).

The tongue members 208 are openable and closable with respect to, i.e., movable toward and away from, each other about the shaft 214. The angle through which the tongue members 208 are opened or closed with respect to each other is detected by an internal sensor 218 and reflected in the opening and closing motion of the gripper 78.

The master arm 200 is displaceable as a whole in the X, Y, and Z directions shown in FIG. 9. The positions of the master arm 200 in the X, Y, and Z directions with respect to the console 20 can be detected by a sensor, not shown. The master arm 200 may be tilted in the X and Y directions with respect to the console 20 by tilting mechanisms. The detected position of the master arm 200 in the X, Y, and Z directions with respect to the console 20 are reflected in the absolute coordinates of the distal-end working unit 46. The master arm 200 is thus capable of indicating six parameters with respect to the position and orientation of the distal-end working unit 46, and also of instructing the gripper 78 to be opened and closed.

When the master arm 200 is released from the operator's hands, the master arm 200 may be returned to its home position shown in FIG. 9 under the bias of resilient members, not shown, with the robot arms 18*a*, 18*b*, 18*c* being kept in their displaced positions.

In the tool coordinate operation mode, the distal-end working unit 46 may be moved along another coordinate axis Zt or in directions along the coordinate axis Zt or in a combination of those directions. In the tool coordinate operation mode, when the master arm 200 is operated, the directions in which the distal-end working unit 46 moves laterally, i.e., the X directions in FIG. 9, correspond to a coordinate axis Xt, the directions in which the distal-end working unit 46 moves back and forth, i.e., the Y directions in FIG. 9, correspond to a coordinate axis Yt, and the directions in which the distal-end working unit 46 moves vertically, i.e., in the Z directions in FIG. 9, correspond to a coordinate axis Zt.

In the tool coordinate operation mode, the posture of the robot arm 18*c* may be determined by setting the position and posture of the distal-end working unit 46, defining the position of the hypothetical reference point P1, and performing known matrix transform calculations. The distal-end working unit 46 may also be operated in the tool coordinate operation mode with the joystick 80*c* or the master arm 200.

In the tool coordinate operation mode, the distal-end working unit 46 can easily be operated to retract an organ in the body cavity 27.

The trackball 84*a* serves as an input means for operating the first intermediate joint 58 of the manipulator 10*c*.

Based on an input action of the trackball 84*a* in an intermediate joint operation mode, the manipulator 10*c* coacts with the robot arm 18*c* (including the slide mechanism 26) connected thereto to bend the first intermediate joint 58 with the distal-end working unit 46 being kept in constant position and posture.

Figure 10:
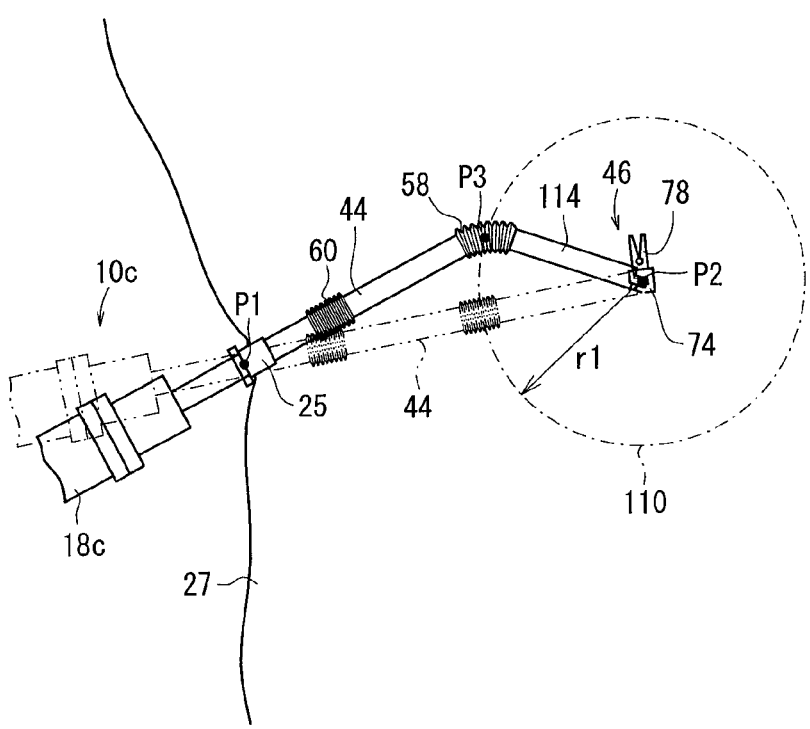
FIG. 10 is a view illustrative of a bending motion of the first intermediate joint in an intermediate joint operation mode.

For example, as shown in FIG. 10, there is assumed a sphere (hypothetical spherical surface) 110 defined around the position P2 of the distal-end joint (the pitch axis 74 and the yaw axis 75) of the distal-end working unit 46 at the time, the sphere 110 having a radius equal to the distance r1 from the position P2 to the first intermediate joint 58, and the first intermediate joint 58 (indicated by a point P3 in FIGS. 10 and 11) is moved along the surface of the sphere 110 from an imaginary-line position to a solid-line position. At this time, the position of the hypothetical reference point P1 at the trocar 25 and the position and posture of the distal-end working unit 46 are kept constant.

If the first intermediate joint 58 can be bent either vertically or laterally only, then the first intermediate joint 58 may be moved along a given hypothetical arc instead of the sphere 110.

Figure 11:
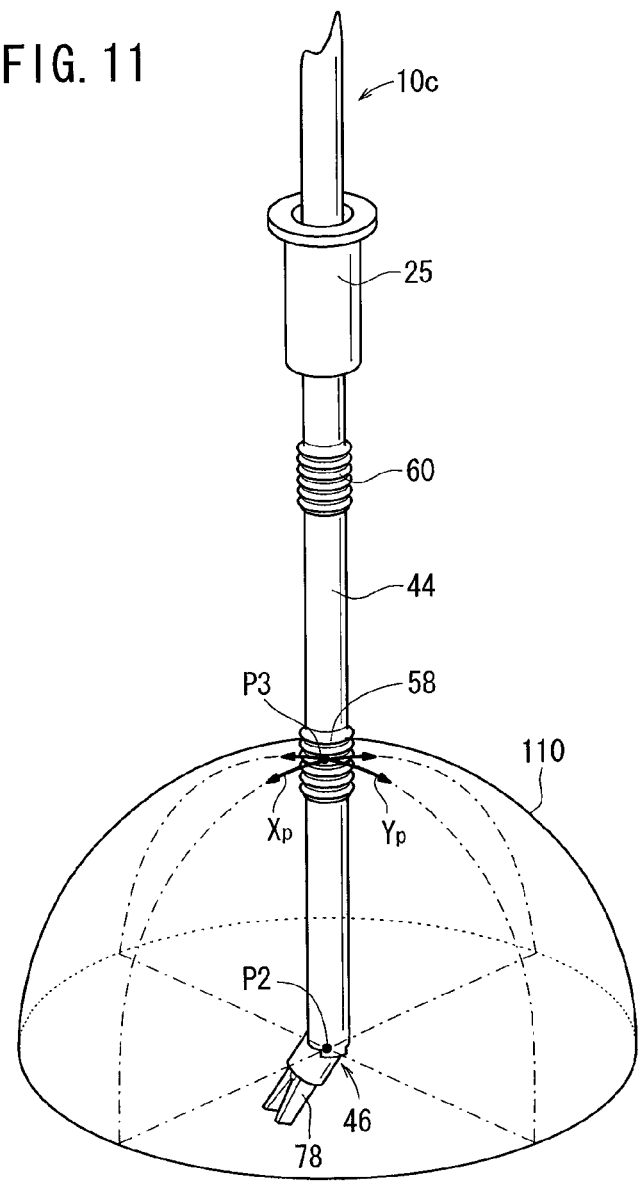
FIG. 11 is a view illustrative of a hypothetical hemisphere used as a reference for bending the first intermediate joint in the intermediate joint operation mode.

In the intermediate joint operation mode, as shown in FIG. 11, orthogonal coordinate axes Xp, Yp extending across the first intermediate joint 58 along the sphere 110 are established based on the orientation of the distal-end working unit 46 or the orientation of the overall manipulator 10*c* at the time. At this time, when the trackball 84*a* is operated, the directions in which it is angularly moved laterally correspond to the coordinate axis Xp, and the directions in which it is angularly moved back and forth correspond to the coordinate axis Yp. The first intermediate joint 58 is also bendable in all directions other than the coordinate axes Xp, Yp. When the trackball 84*a* is angularly moved in a given direction, the first intermediate joint 58 is bent depending on the direction in which the trackball 84*a* is angularly moved and the angular amount by which the trackball 84*a* is angularly moved. When the trackball 84*a* is stopped, the first intermediate joint 58 stops being bent. When the first intermediate joint 58 reaches a limit of its bending range in a given direction, a bending command for bending the first intermediate joint 58 further in that direction is disabled.

In the intermediate joint operation mode, another rotary input means may be employed rather than the trackball 84*a*. For example, the joystick 80*c* may be employed such that the directions in which it is tilted laterally correspond to the coordinate axis Xp and the directions in which it is tilted back and forth correspond to the coordinate axis Yp.

In the intermediate joint operation mode, the posture of the robot arm 18*c* may be determined by setting the position and posture of the distal-end working unit 46, defining the positions of the hypothetical reference point P1 and the first intermediate joint 58, and performing known matrix transform calculations.

For operating the first intermediate joint 58, the enable switch 86*a* is pressed to enable the trackball 84*a*. If the enable switch 86*a* is not pressed, then the trackball 84*a* remains disabled, and the first intermediate joint 58 is prevented from being moved when the trackball 84*a* is operated carelessly.

When the return switch 88*a* is pressed, the first intermediate joint 58 automatically returns to a zero-bend-angle state (see FIG. 2) at a predetermined speed. With the first intermediate joint 58 in the zero-bend-angle state, the joint shaft 44 can easily be pulled out of the trocar 25. The return switch 88*a* is a momentary switch which is enabled only when it is pressed. When the return switch 88*a* is released, the returning motion of the first intermediate joint 58 is interrupted, allowing the operator to confirm the state of the first intermediate joint 58.

In the intermediate joint operation mode, the second intermediate joint 60 can also be bent by the trackball 84*b*, the enable switch 86*b*, and the return switch 88*b*. The trackball 84*b*, the enable switch 86*b*, and the return switch 88*b* operate in the same manner as the trackball 84*a*, the enable switch 86*a*, and the return switch 88*a*.

Figure 12:
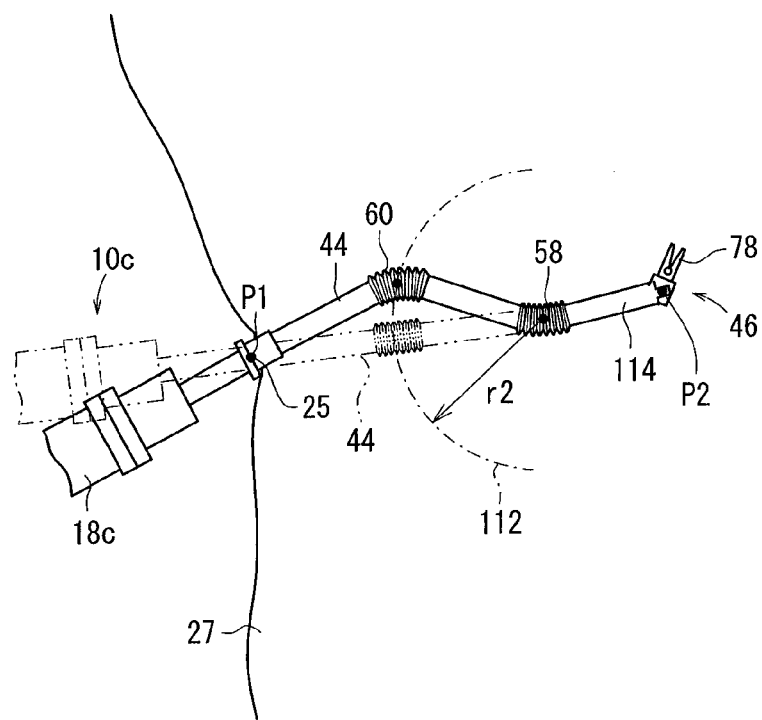
FIG. 12 is a view illustrative of a bending motion of the second intermediate joint according to a first control process in the intermediate joint operation mode.

The second intermediate joint 60 can be controlled according to a plurality of control processes, which can be selected. According to a first control process, as shown in FIG. 12, there is assumed a sphere 112 around the first intermediate joint 58, the sphere 112 having a radius equal to the distance r2 from the first intermediate joint 58 to the second intermediate joint 60, and the second intermediate joint 60 is moved along the surface of the sphere 112 from an imaginary-line position to a solid-line position. At this time, the position of the hypothetical reference point P1 at the trocar 25, the position and posture of the distal-end working unit 46, and the position and posture of a link 114 extending from the point P2 to the first intermediate joint 58 are kept constant. According to the first control process, the first intermediate joint 58 is also bent in coaction with the second intermediate joint 60 as it is bent.

Figure 13:
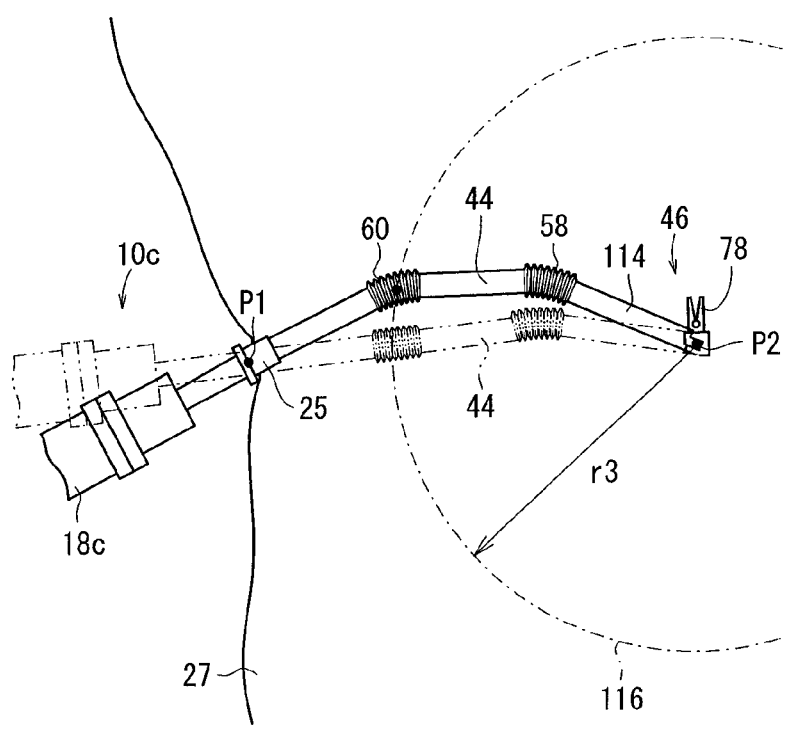
FIG. 13 is a view illustrative of a bending motion of the second intermediate joint according to a second control process in the intermediate joint operation mode.

According to a second control process, as shown in FIG. 13, there is assumed a sphere 116 defined around the position P2 of the distal-end joint (the pitch axis 74 and the yaw axis 75) of the distal-end working unit 46 at the time, the sphere 116 having a radius equal to the distance r3 from the position P2 to the second intermediate joint 60, and the second intermediate joint 60 is moved along the surface of the sphere 116 from an imaginary-line position to a solid-line position. At this time, the position of the hypothetical reference point P1 at the trocar 25 and the position and posture of the distal-end working unit 46 are kept constant. According to the second control process, the first intermediate joint 58 remains bent.

The first intermediate joint 58 and the second intermediate joint 60 may automatically be moved according to a program or a teaching process, rather than being controlled based on the operation of the trackballs 84*a*, 84*b*.

Operation of the manipulator 10*c* and the medical robot system 12 thus constructed will be described below.

First, a gas is introduced around the affected region of the patient to form the body cavity 27, and the distal-end working units 46 and the joint shaft 44 of the manipulator 10*c* are inserted through the trocar 25. The state in the body cavity 27 is confirmed based on an endoscopic image captured by the endoscope 24 that has been inserted into the body cavity 27.

Prior to a surgical technique to be performed on an affected region 118, other organs that exist around the affected region 118 are retracted to given regions to provide a wide operative field in the body cavity 27.

Figure 14:
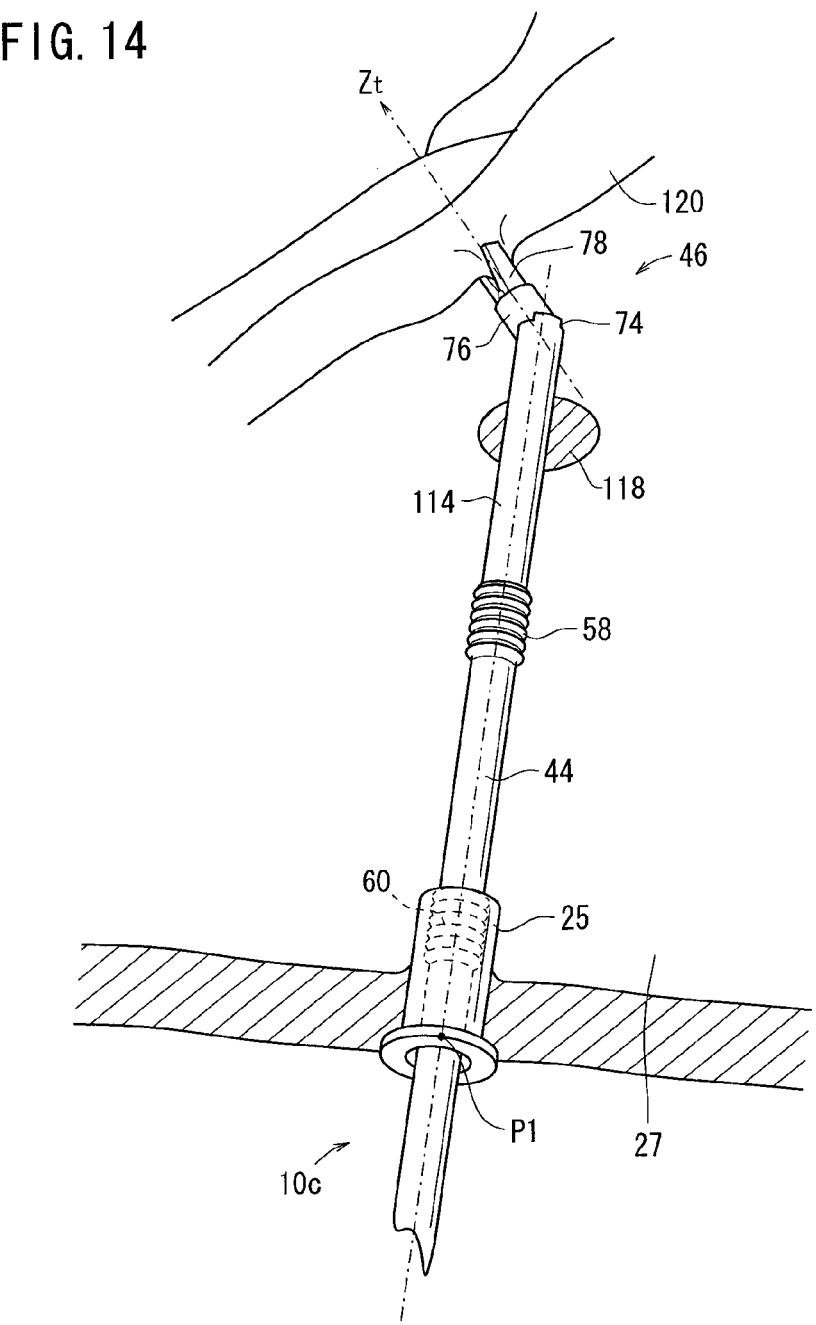
FIG. 14 is a perspective view showing the manner in which a gripper of the manipulator grips a large intestine.

For example, as shown in FIG. 14, for retracting a large intestine 120, the distal-end working unit 46 is bent around the pitch axis 74 and the yaw axis 75 into an orientation substantially perpendicularly to an appropriate portion of the large intestine 120. Thereafter, the gripper 78 grips the large intestine 120 lightly.

Figure 15:
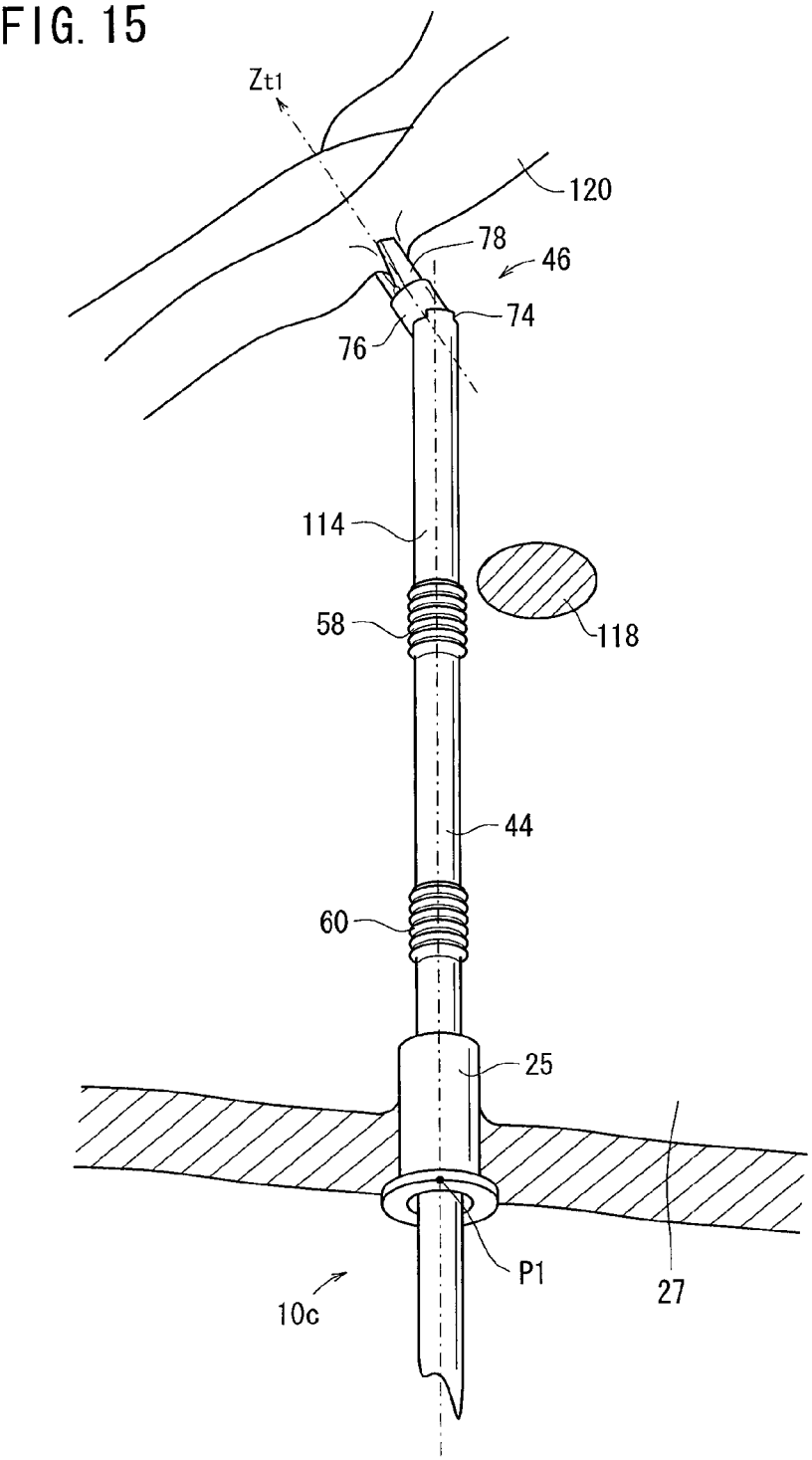
FIG. 15 is a perspective view showing the manner in which the gripper of the manipulator retracts the large intestine.

Then, as shown in FIG. 15, the distal-end working unit 46 is moved forward to retract the large intestine 120 to a deeper region. At this time, in order to keep the distal-end working unit 46 and the gripped portion of the large intestine 120 oriented relatively to each other, the distal-end working unit 46 may be pushed in the direction of a coordinate axis Zt1 in the tool coordinate operation mode (see FIG. 8).

By thus retracting the large intestine 120, the large intestine 120 is sufficiently spaced from the affected region 118, allowing the surgeon to perform a surgical operation on the affected region 118. The manipulator 10*c* thus acts as a retractor. In some instances, even when the large intestine 120 is retracted away from the affected region 118 by the manipulator 10*c*, the manipulator 10*c* may be positioned across the body cavity 27, failing to provide a wide operative field in the body cavity 27.

To avoid the above difficulty, at least one of the first intermediate joint 58 and the second intermediate joint 60 of the manipulator 10*c* is bent.

Figure 16:
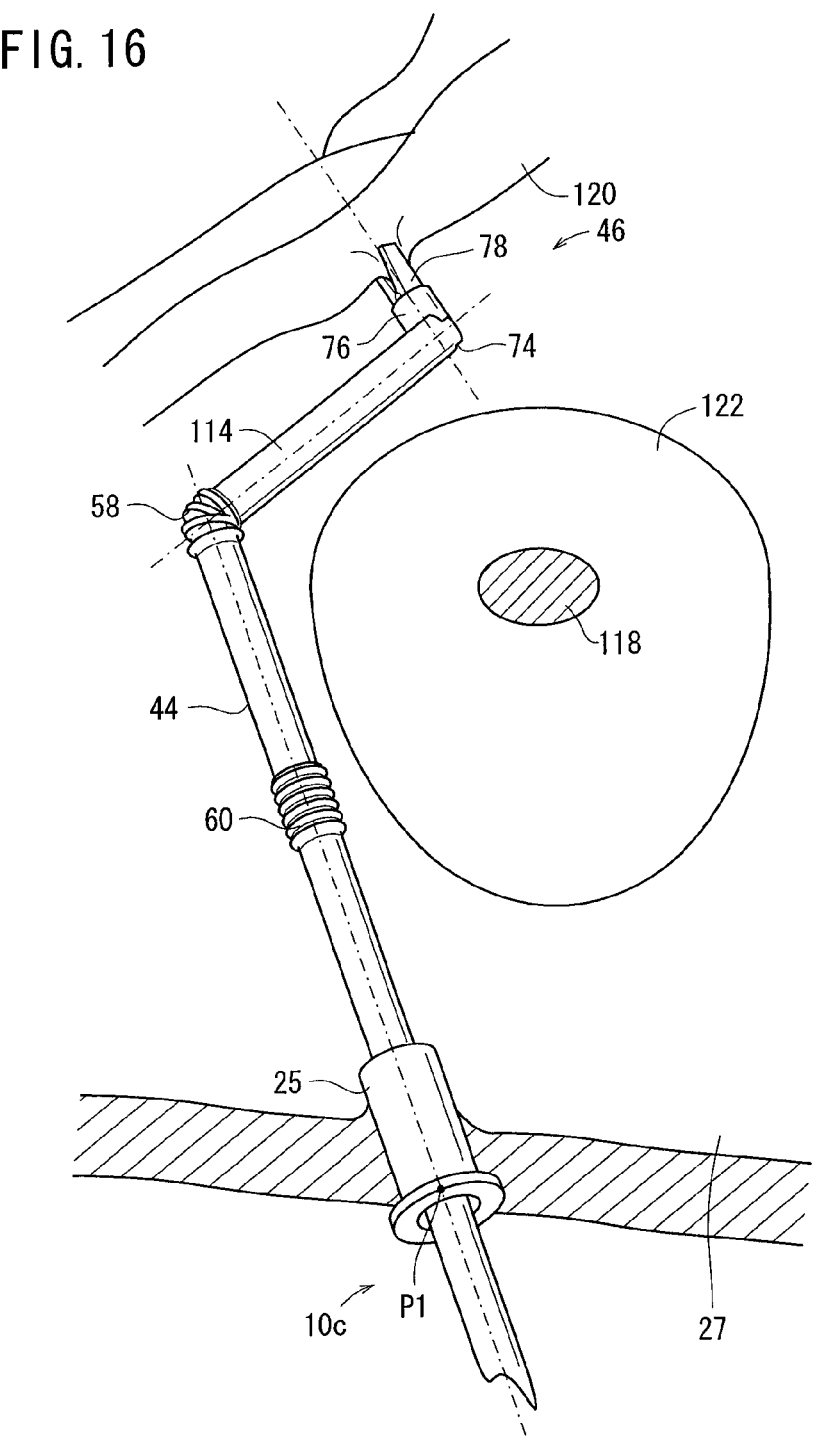
FIG. 16 is a perspective view showing the manner in which the first intermediate joint is bent.

For example, as shown in FIG. 16, in the intermediate joint operation mode, the first intermediate joint 58 is bent to make the link 114 substantially parallel to the large intestine 120. Thus, the joint shaft 44 is spaced from the affected region 118, providing a wide operative field 122 around the affected region 118. The surgeon finds it easy to perform a surgical procedure on the affected region 118 with the other manipulators 10*a*, 10*b*. As a result, the time required to perform the surgical operation may be shortened.

Figure 17:
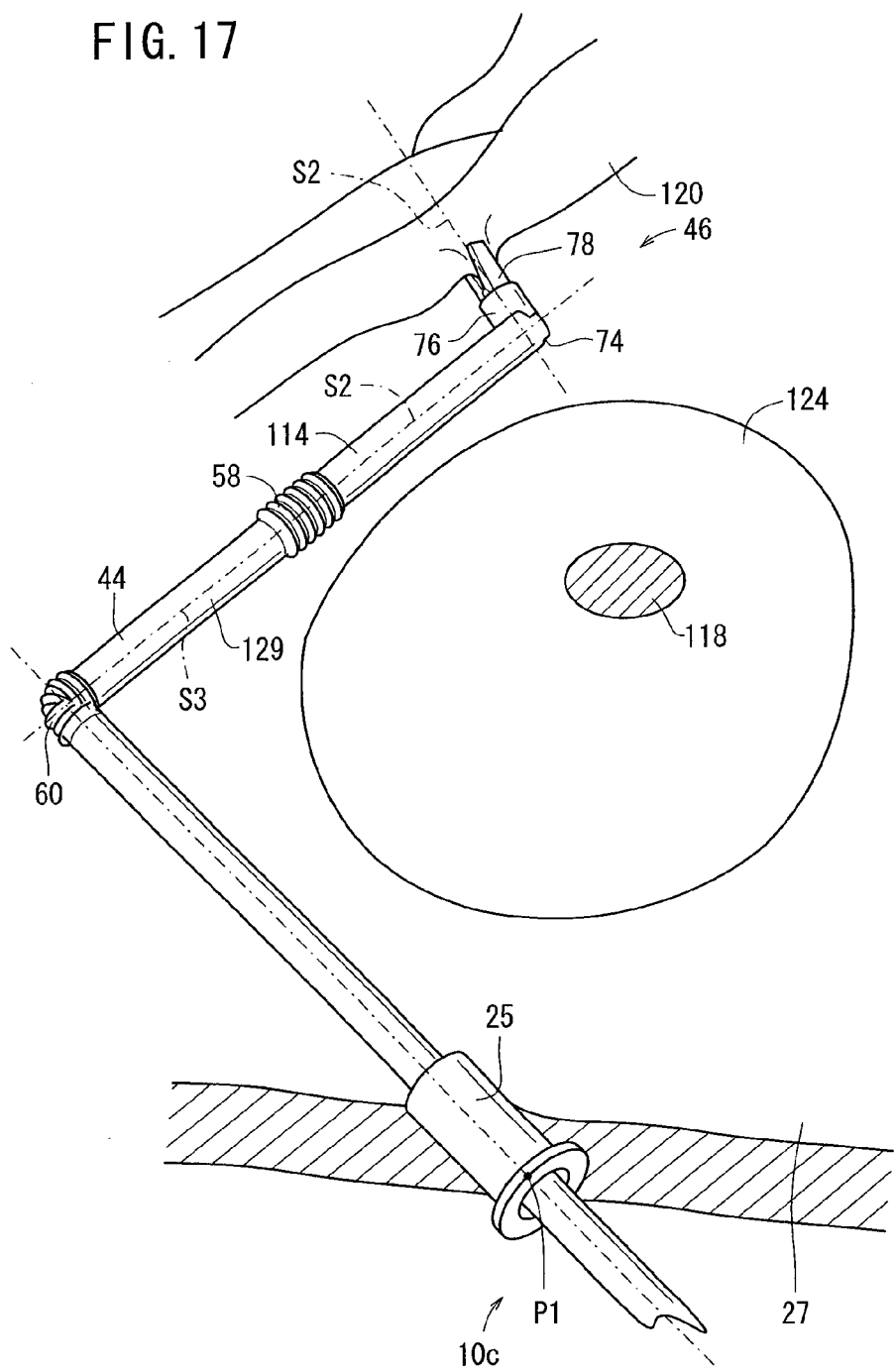
FIG. 17 is a perspective view showing the manner in which the second intermediate joint is bent.
Figure 18:
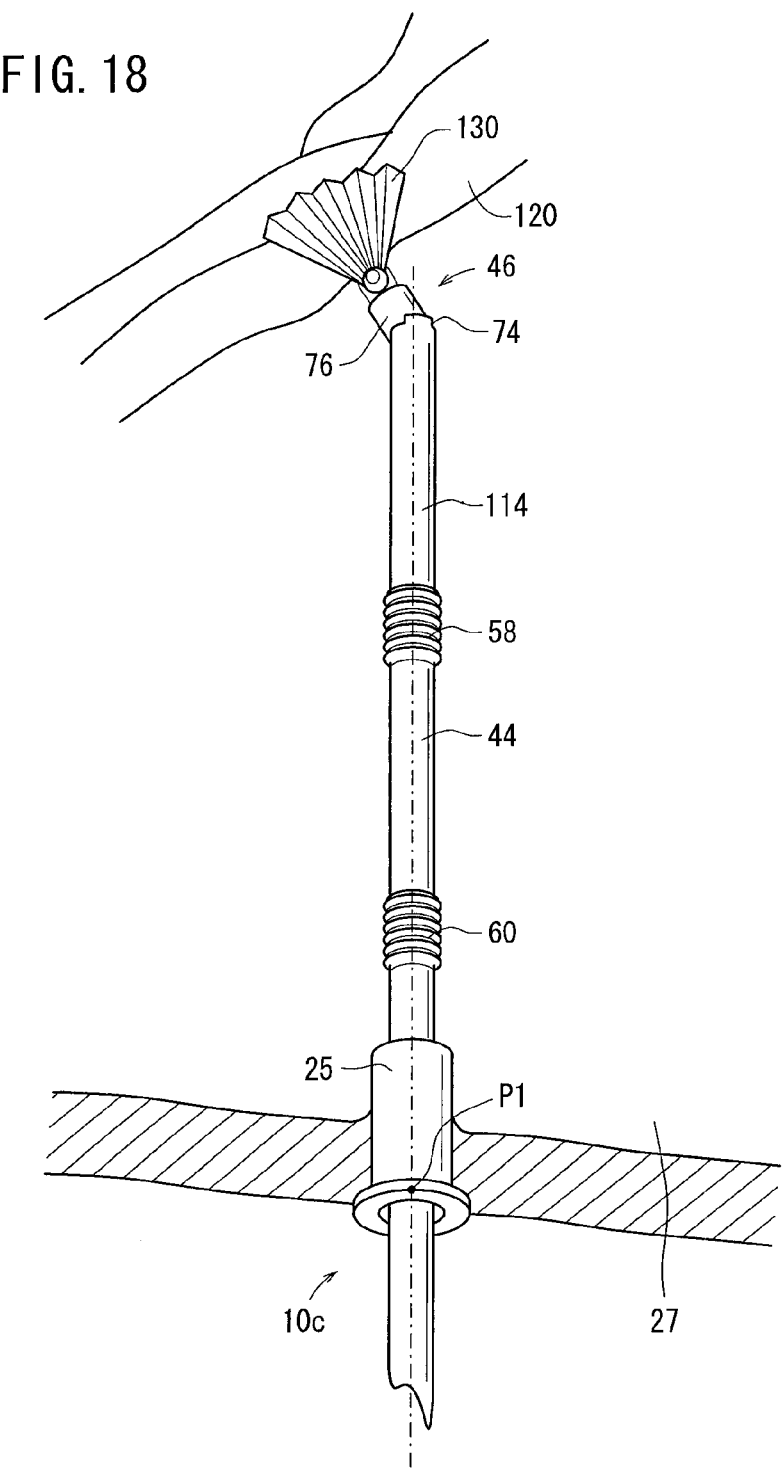
FIG. 18 is a perspective view of a distal-end action unit having a fan-like mechanism.

Although the wide operative field 122 is provided simply by bending the first intermediate joint 58, the second intermediate joint 60 may instead be bent to provide a wider operative field 124, as shown in FIG. 17. For bending the second intermediate joint 60, one or both of the first control process (see FIG. 12) and the second control process (see FIG. 13) may be carried out.

In this case, it is assumed that the distal-end working unit 46 has an axis S1, the link 114 has an axis S2, and a link 129 extending from the first intermediate joint 58 to the second intermediate joint 60 has an axis S3. The second intermediate joint 60 may be bent such that the axes S2, S3 are held in alignment with each other.

For retracting the large intestine 120, it may not be gripped by the gripper 78, but may be engaged and pushed by a distal-end action unit 130 (see FIG. 18) having a folding-fan-like mechanism. The distal-end action unit 130 may comprise a membrane extending between two openable gripper arms. Since the distal-end action unit 130 does not grip the large intestine 120, it is less detrimental to the large intestine 120. When the distal-end action unit 130 is folded by closing the openable gripper arms, it can easily be inserted through the trocar 25.

With the manipulator 10*c* according to the present embodiment, the gripper 78 can be adjusted in orientation about the pitch axis 74 and the yaw axis 75 of the distal-end joint for performing an appropriate surgical procedure on the affected region. If the manipulator 10*c* is used as a retractor, then the gripper 78 can appropriately be oriented to an organ such as the large intestine 120. Furthermore, since the joint shaft 44 of the manipulator 10*c* can be bent at the first intermediate joint 58 and the second intermediate joint 60, the joint shaft 44 can be appropriately placed around the affected region to provide a wide operative field in the body cavity 27. Particularly, the bendable joint shaft 44 is preferable to avoid physical interference with the other manipulators 10*a*, 10*b* in the body cavity 27.

The manipulator 10*c* is connected to the robot arm 18*c*, and the robot arm 18*c* coacts with the manipulator 10*c* to move the manipulator 10*c* back and forth and tilt the manipulator 10*c* with respect to the reference point P1 at the trocar 25 for achieving appropriate manipulator motions.

With the medical robot system 12 according to the present embodiment, the manipulator 10*c* is used to retract an organ or organs in the body cavity 27 to a given region to provide a wide operative field in the body cavity 27. Inasmuch as the joint shaft 44 is bendable at the first intermediate joint 58 and the second intermediate joint 60, the joint shaft 44 can appropriately be positioned in the body cavity 27 to provide a wider operative field in the body cavity 27 and also to avoid physical interference with the other manipulators 10*a*, 10*b* for allowing the surgeon to perform a surgical procedure with ease.

The first intermediate joint 58 and the second intermediate joint 60 are movable on a hypothetical sphere or a hypothetical arc around a given reference point depending on the angular amount by which and the direction in which the trackballs 84a, 84b are angularly moved. The trackballs 84a, 84b allow the operator to bend the first intermediate joint 58 and the second intermediate joint 60 appropriately with ease and also intuitively in a manner to fit the feeling of the operator.

Figure 19:
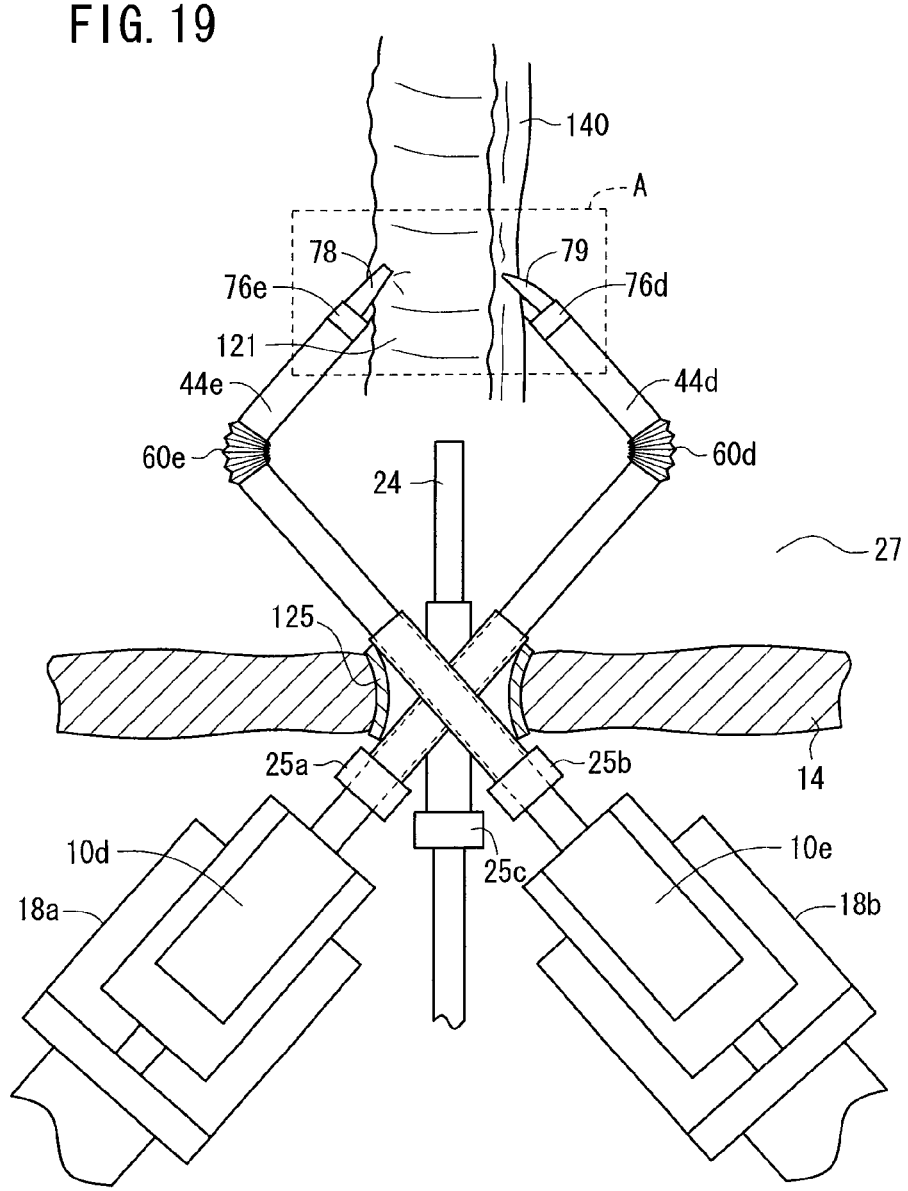
FIG. 19 is a schematic view illustrative of a medical robot system according to a second embodiment of the present invention.

FIG. 19 is a schematic view illustrative of a medical robot system according to a second embodiment of the present invention. FIG. 19 shows manipulators 10d, 10e and an endoscope 24, which are constituent elements of the medical robot system.

The medical robot system according to the second embodiment differs from the medical robot system 10 according to the first embodiment in that the manipulator 10d having a different structure from the manipulator 10a is provided at the distal end of the robot arm 18a and the manipulator 10e having a different structure from the manipulator 10b is provided at the distal end of the robot arm 18b.

A rod-shaped member 44d of the manipulator 10d has an intermediate joint 60d in an intermediate portion thereof, and a rod-shaped member 44e of the manipulator 10e has an intermediate joint 60e in an intermediate portion thereof. The intermediate joints 60d, 60e have the same structure as the first intermediate joint 58 shown in FIGS. 2 and 4. More specifically, the manipulators 10d, 10e have such a structure that the second intermediate joint 60 is eliminated from the manipulator 10 shown in FIG. 2. In the structure shown in FIG. 19, an end effector provided at the distal end of the manipulator 10d is configured as scissors 79, and an end effector provided at the distal end of the manipulator 10e is configured as a gripper 78.

The manipulators 10d, 10e can be operated using operation input means shown in FIG. 7. More specifically, an operator operates joysticks (first and second input means) 80a, 80b to move and open/close distal-end working units 76d, 76e of the manipulators 10d, 10e and change the posture thereof. Further, the operator can operate trackballs 84a, 84b to move the intermediate joints 60d, 60e. Incidentally, the trackballs 84a, 84b may be omitted. In this case, a switch may be provided to select an object(s) to be operated, and the operator may operate the joysticks 80a, 80b to move the intermediate joints 60d, 60e.

As shown in FIG. 19, the manipulators 10d, 10e and the endoscope 24 are inserted into a body cavity 27 of a patient 14 through a common trocar supporting member 125. The operator captures images of an affected region and its peripheral portions with the endoscope 24, while performs a given surgical procedure on the affected region with the end effectors (gripper 78 and scissors 79) provided at the distal end of the manipulators 10d, 10e. That is, the medical robot system according to the second embodiment enables the operator to perform a surgical procedure by single port access.

More specifically, the trocar supporting member 125 has a plurality of holes (three holes in the present embodiment), into which the trocars 25a to 25c are hermetically inserted, respectively. The trocars 25a, 25b are adapted for the manipulators 10d, 10e, whereas the trocar 25c is adapted for the endoscope 24. If the outer diameter of the rod-shaped members 44d, 44e of the manipulators 10d, 10e has the same size as the inner diameter of the endoscope 24, the trocars 25a, 25b and the trocar 25c may have the same structure.

A laparoscopic surgical operation process is performed using the medical robot system according to the second embodiment by single port access in the following manner. First, the trocar supporting member 125 is inserted into the patient 14. Next, the trocars 25a, 25b for the manipulators 10d, 10e and the trocar 25c for the endoscope 24 are inserted into the trocar supporting member 125. Then, the two manipulators 10d, 10e and the endoscope 24 are inserted into the body cavity 27 of the patient 14 through the trocars 25a, 25b, 25c, respectively. In this case, as shown in FIG. 19, the rod-shaped members 44d, 44e of the manipulators 10d, 10e are straightened, and then they are inserted such that the rod-shaped members 44d, 44e intersect with each other.

After the rod-shaped members 44d, 44e are inserted to a certain extent, the intermediate joints 60d, 60e are bent in such a direction that the end effectors (gripper 78 and scissors 79) approach each other. Next, an observing point of the endoscope 24 is secured in order that images of a portion to be treated and the distal-end working units 76d, 76e can be captured with the endoscope 24. Then, the operator performs a given surgical procedure on the portion to be treated, with the end effectors. In a surgical example shown in FIG. 19, a tissue 121 within the body cavity 27 is gripped with the gripper 78, while a membranous tissue 140 near the tissue 121 is cut out with the scissors 79.

With the medical robot system according to the second embodiment, when a surgical procedure is performed by single port access, the distal-end working units 76 having the end effectors can be moved closer to each other by bending the rod-shaped members 44d, 44e of the two manipulators 10d, 10e which intersect with each other at the trocar supporting member 125, by means of the intermediate joints 60d, 60e. Thus, a surgical procedure by single port access can be performed suitably.

As shown in FIG. 19, when the rod-shaped members 44d, 44e of the manipulators 10d, 10e intersect with each other, the proximal end portion of the manipulator 10d is located on the left side, while the proximal end portion of the manipulator 10e is located on the right side. Accordingly, the positional relation of the proximal end portions is opposite to the positional relation of the distal-end working units 76d, 76e. For easier understanding, the field of view of the endoscope 24 (image captured with the endoscope 24), i.e., the area that is displayed on the screen of the monitor 82 (see FIG. 1), is represented by reference character A. As described above, the proximal end of the manipulator 10d is located on the left side whereas the distal-end working unit 76d of the manipulator 10d is located on the right side on the screen of the monitor 82. Similarly, the proximal end of the manipulator 10e is located on the right side whereas the distal-end working unit 76e of the manipulator 10e is located on the left side on the screen of the monitor 82.

If the left joystick 80a in FIG. 7 always serves to operate the left manipulator 10d and the right joystick 80b always serves to operate the right manipulator 10e, an operator has to operate the joysticks 80a, 80b while imagining a positional relation that is left-and-right reverse to the positional relation of the distal-end working units 76d, 76e on the screen. Accordingly, the operator can not operate the manipulators intuitively.

Thus, when the manipulators 10d, 10e are inserted into the body cavity 27 such that the rod-shaped members 44d, 44e intersect with each other, the console 20 (see FIG. 1) may control operation of the manipulators 10d, 10e in a left-and-right reverse operation mode to be described below. In the left-and-right reverse operation mode, the console 20 operates the manipulator 10e whose distal-end working unit 76e is located on the left side on the screen of the monitor 82, based on input operation of the left joystick 80a, while the console 20 operates the manipulator 10d whose distal-end working unit 76d is located on the right side on the screen of the monitor 82, based on input operation of the right joystick 80b.

By setting the left-and-right reverse operation mode, even if the manipulators 10d, 10e are inserted into the body cavity 27 with the rod-shaped members 44d, 44e intersecting with each other, the operator can operate the manipulators intuitively in a manner to fit the feeling of the operator, because operation by the left hand of the operator is reflected on the movement of the manipulator 10e whose distal-end working unit 76e is located on the left side on the screen, and operation by the right hand of the operator is reflected on the movement of the manipulator 10d whose distal-end working unit 76d is located on the right side on the screen.

In this case, a switch may be provided onto the console 20, for enabling/disabling the left-and-right reverse operation mode, and the operator may manually operate the switch to cause the console to control operation of the manipulators in the left-and-right reverse operation mode.

Alternatively, the console 20 may determine whether the rod-shaped members 44d, 44e intersect with each other or not, based on the positional coordinates of the manipulators 10d, 10e, and when the console 20 determines that the rod-shaped members 44d, 44e intersect with each other, the console 20 may automatically set the left-and-right reverse operation mode. In this case, the operator does not need to determine by oneself whether the rod-shaped members 44d, 44e intersect with each other or not, and burden on the operator is thus reduced.

Figure 20:
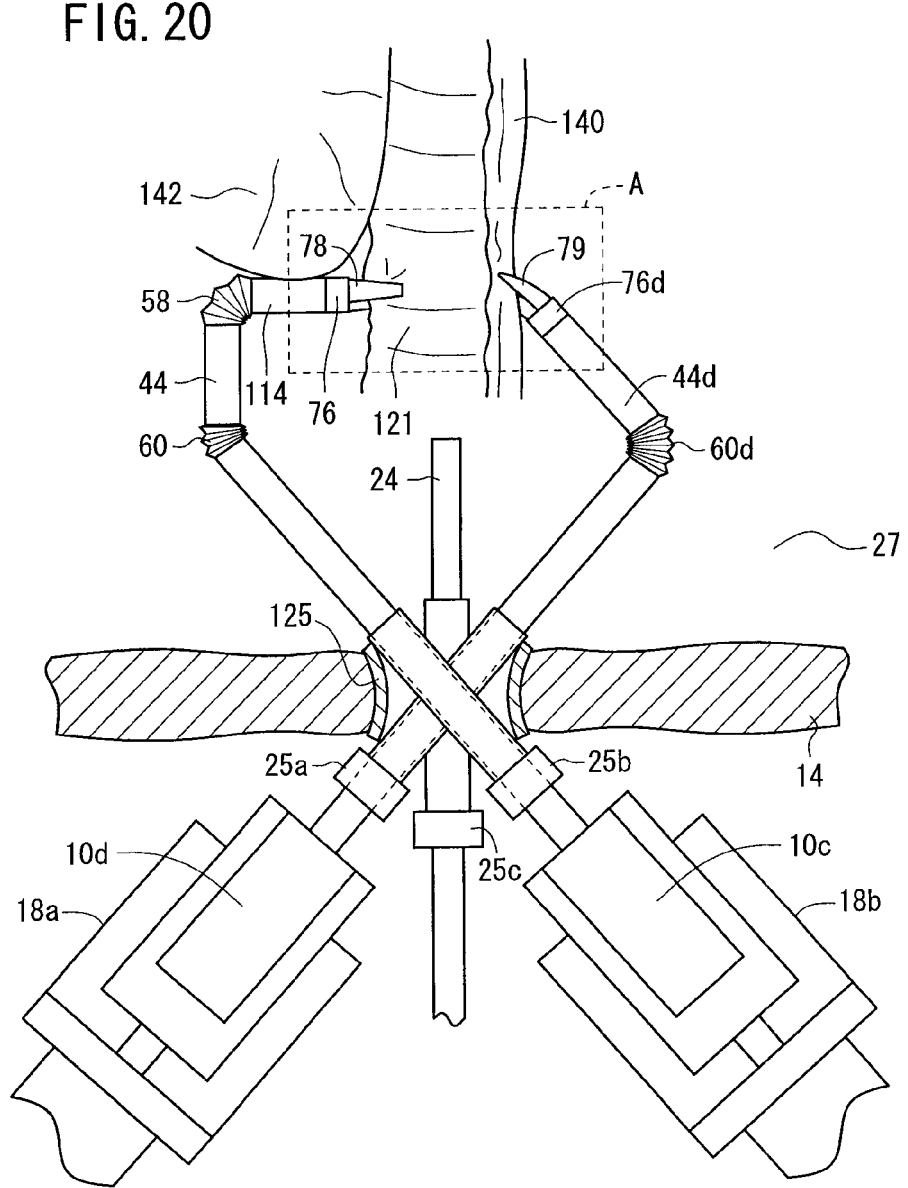
FIG. 20 is a schematic view illustrative of a medical robot system according to a third embodiment of the present invention.

FIG. 20 is a schematic view illustrative of a medical robot system according to a third embodiment of the present invention. FIG. 20 shows manipulators 10c, 10d and an endoscope 24, which are constituent elements of the medical robot system.

The medical robot system according to the third embodiment is a medical robot system in which the manipulator 10c (see FIG. 2) of the medical robot according to the first embodiment, instead of the manipulator 10e, is applied to the medical robot system according to the second embodiment. The manipulator 10d that is provided at the distal end of the robot arm 18a has the same structure as the manipulator 10d according to the second embodiment.

As described above, the manipulator 10c has the first intermediate joint 58 and the second intermediate joint 60, and accordingly the rod-shaped member 44 can be bent at two points. Thus, the manipulator 10c has greater flexibility to its possible shape, compared to the manipulator 10e (see FIG. 19). The trocar supporting member 125 and the trocars 25a to 25c have the same structures as the trocar supporting member 125 and the trocars 25a to 25c shown in FIG. 19, respectively.

Figure 21:
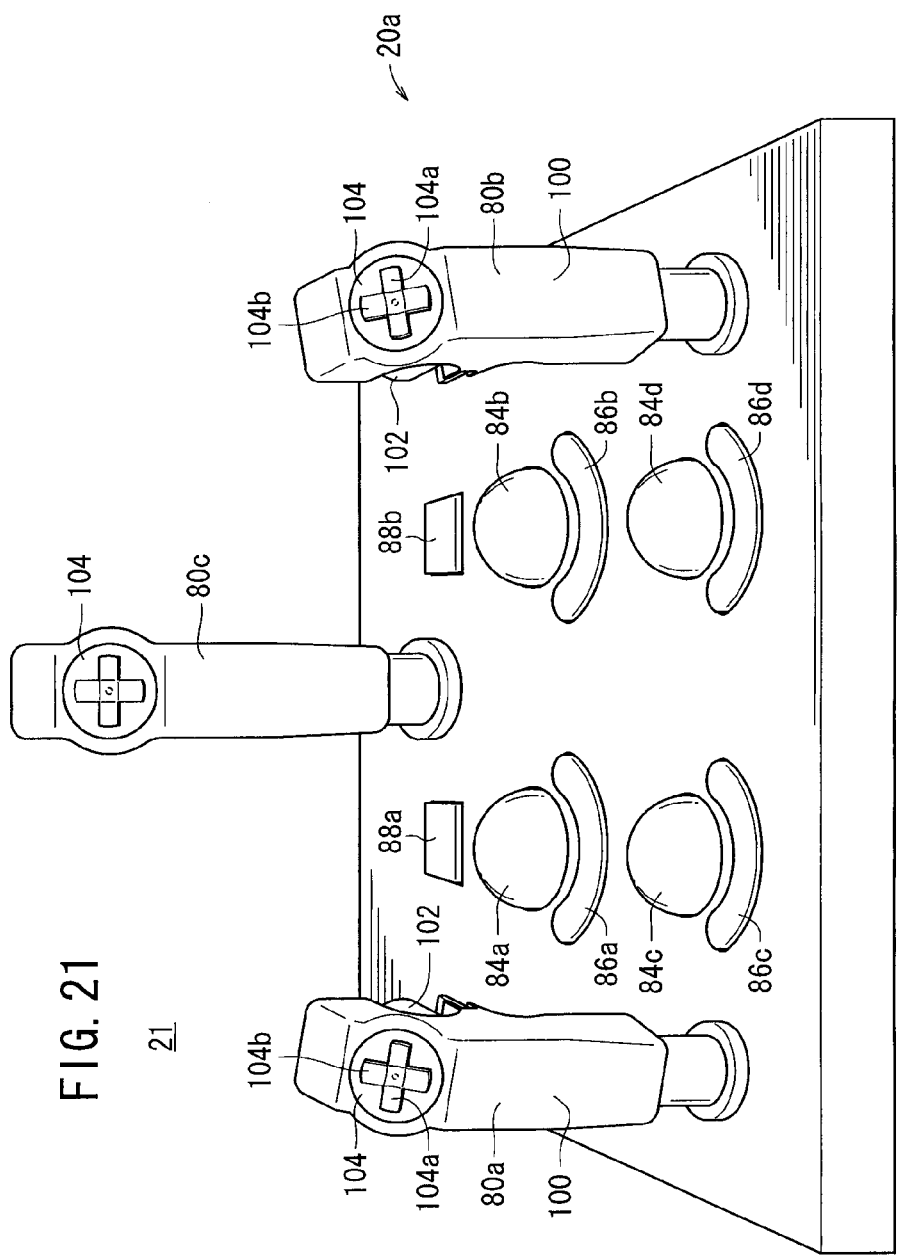
FIG. 21 is a schematic perspective view of a console of the medical robot system according to the third embodiment.

The manipulators 10c, 10d can be operated by means of operation input means 21 of a console 20a shown in FIG. 21. The console 20a having the operation input means 21 differs from the console 20 shown in FIG. 7 in that the console 20a further comprises two trackballs 84c, 84d and two enable switches 86c, 86d. More specifically, an operator can operate the joysticks 80a, 80b to move and open/close distal-end working units 76, 76d of the manipulators 10c, 10d and change the posture thereof, and also operate the trackballs 84a to 84d to actuate the intermediate joint 60d, the first intermediate joint 58 and the second intermediate joint 60.

The console 20a can execute the left-and-right reverse operation mode, as with the console 20 according to the second embodiment. Accordingly, when the manipulators 10c, 10d intersect with each other, the manipulator 10c whose distal-end working unit 76 is located on the left side is operated based on input operation by the left joystick 80a, and the manipulator 10d whose distal-end working unit 76d is located on the right side is operated based on input operation by the right joystick 80b. In this case, one (e.g., trackball 84a at the back) of the two left trackballs 84a, 84c serves to operate the first intermediate joint 58, while the other trackball (e.g., trackball 84c at the front) serves to operate the second intermediate joint 60. Further, one of the two right trackballs 84b, 84d serves to operate the intermediate joint 60d.

When the manipulators 10c, 10d do not intersect with each other, the manipulator 10d is operated based on input operation by the left joystick 80a, while the manipulator 10c is operated based on input operation by the right joystick 80b. In this case, one of the two left trackballs 84a, 84c serves to operate the intermediate joint 60d. Also, one (e.g., trackball 84b at the back) of the two right trackballs 84b, 84d serves to operate the first intermediate joint 58, and the other trackball (e.g., trackball 84d at the front) serves to operate the second intermediate joint 60.

Incidentally, as with the operation input means of the console 20 shown in FIG. 7, the trackballs 84a, 84b may be provided on the left side and on the right side, respectively. In this case, a switch may be provided to select an object to be operated based on input operation by each of the trackballs 84a, 84b. For example, the switch may be configured such that the operator can switch between one mode where operation by the trackball 84a (or the trackball 84b) is reflected on the movement of the intermediate joint 60d and another mode where operations by the trackballs 84a, 84b are reflected on the movements of the first and second intermediate joints 58, 60, respectively.

A laparoscopic surgical operation process is performed using the medical robot system according to the third embodiment by single port access in the following manner. First, the trocar supporting member 125 is inserted into the patient 14. Next, the trocars 25a, 25b for the manipulators 10c, 10d and the trocar 25c for the endoscope 24 are inserted into the trocar supporting member 125. Then, the two manipulators 10c, 10d and the endoscope 24 are inserted into the body cavity 27 of the patient 14 through the trocars 25a, 25b, 25c, respectively. In this case, as shown in FIG. 20, the rod-shaped members 44, 44d of the manipulators 10c, 10d are straightened, and then they are inserted such that the rod-shaped members 44, 44d intersect with each other.

After the rod-shaped members 44, 44d are inserted to a certain extent, the first and second intermediate joints 58, 60 of the manipulator 10c are bent, so that an organ 142 (obstacle to an operative field) is pushed aside (retracted) with the rod-shaped member 44 (link 114 in FIG. 20) for a wider operative field. After the wider operative field has been thus secured, the intermediate joint 60d of the rod-shaped member 44d are bent and the first and second intermediate joints 58, 60 are further bent so as to move the end effectors closer to each other.

Next, an observing point of the endoscope 24 is secured in order that images of a portion to be treated and the distal-end working units 76, 76d can be captured with the endoscope 24. Then, the operator performs a given surgical procedure on the portion to be treated, with the end effectors. In a surgical example shown in FIG. 20, a tissue 121 within the body cavity 27 is gripped with the gripper 78, while a membranous tissue 140 near the tissue 121 is cut out with the scissors 79.

With the medical robot system according to the third embodiment, the distal-end working units 76, 76d having the end effectors can be moved closer to each other by operation of the intermediate joint 60d and the first and second intermediate joints 58, 60. Thus, in the third embodiment, a surgical procedure can be performed suitably by single port access, as in the second embodiment.

Also, with the third embodiment, the manipulator 10c serving as a retractor performs an operation (e.g., gripping) on an affected region with the end effector provided at the distal end thereof, while the manipulator 10c pushes aside the organ 142

(obstacle to the operative field) with the rod-shaped member 44 having a plurality of intermediate joints. In this manner, one manipulator 10c doubles as a forceps and a retractor. As a result, a surgical procedure can be performed using a smaller number of manipulators. Also, the trocar for a retractor can be omitted, and thus a much less-invasive surgery can be achieved.

Although certain preferred embodiments of the present invention have been shown and described in detail, it should be understood that various changes and modifications may be made therein without departing from the scope of the appended claims.

What is claimed is:
1. A medical robot system comprising:
a plurality of first robot arms supporting respective manipulators thereon;
a second robot arm supporting an endoscope thereon;
a controller for controlling said first robot arms and said second robot arm;
a monitor for displaying an image captured with said endoscope;
first input means which is operated by the left hand of an operator; and
second input means which is operated by the right hand of said operator,
said manipulators and said endoscope being inserted into a body cavity through a common trocar supporting member,
wherein each of said manipulators includes a rod-shape member for insertion through said trocar supporting member into said body cavity, a distal-end working unit mounted on a distal end of said rod-shaped member and having at least one joint, and at least one intermediate joint disposed in said rod-shaped member for bending said rod-shaped member,
wherein the intermediate joint allows the rod-shaped member of each of the manipulators to bend to form an outer convex shape so that the intermediate joints of the manipulators are positioned away from each other, in a state where the first robot arms support the manipulators outside the body cavity so that the rod-shaped members of the manipulators cross each other inside the trocar supporting member;
wherein said controller is adapted to detect a condition in which said rod-shaped members of said manipulators cross each other inside the trocar supporting member such that the image displayed on said monitor shows said manipulator having a proximal end located on the right side outside the body cavity in the image and an end effector located on the left side in the image, and said manipulator that has a proximal end located on the left side outside the body cavity in the image and an end effector located on the right side in the image;
wherein said controller is adapted to, upon detection of the condition, set a reverse operation mode in which said manipulator having a proximal end located on the right side outside the body cavity in the image is operated based on input operation by said first input means and said manipulator having a proximal end located on the left said outside the body cavity in the image is operated based on input operation by said second input means.

2. A medical robot system according to claim 1, wherein at least one of said manipulators serves as a retractor, and said rod-shaped member of said at least one manipulator serving as the retractor includes a plurality of said intermediate joints.

* * * * *